(12) United States Patent
Hazen et al.

(10) Patent No.: US 9,168,233 B2
(45) Date of Patent: Oct. 27, 2015

(54) TREATMENT AND PREVENTION OF CARDIOVASCULAR DISEASE AND THROMBOSIS

(71) Applicant: The Cleveland Clinic Foundation, Cleveland, OH (US)

(72) Inventors: Stanley L. Hazen, Pepper Pike, OH (US); Bruce Levison, Twinsburg, OH (US); Zeneng Wang, Shaker Heights, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 13/915,299

(22) Filed: Jun. 11, 2013

(65) Prior Publication Data

US 2013/0345171 A1    Dec. 26, 2013

Related U.S. Application Data

(60) Provisional application No. 61/658,208, filed on Jun. 11, 2012.

(51) Int. Cl.

| | |
|---|---|
| *A61K 31/045* | (2006.01) |
| *A61K 31/66* | (2006.01) |
| *A61K 31/205* | (2006.01) |
| *A61K 31/695* | (2006.01) |
| *A61K 45/06* | (2006.01) |
| *A61K 31/22* | (2006.01) |
| *A23L 1/30* | (2006.01) |
| *A23L 2/52* | (2006.01) |
| *A61K 31/133* | (2006.01) |
| *A61K 31/663* | (2006.01) |

(52) U.S. Cl.
CPC ............... *A61K 31/045* (2013.01); *A23L 1/30* (2013.01); *A23L 2/52* (2013.01); *A61K 31/133* (2013.01); *A61K 31/205* (2013.01); *A61K 31/22* (2013.01); *A61K 31/66* (2013.01); *A61K 31/663* (2013.01); *A61K 31/695* (2013.01); *A61K 45/06* (2013.01)

(58) Field of Classification Search
CPC ... A61K 31/045; A61K 31/66; A61K 31/205; A61K 31/695; A61K 45/06; A61K 31/22; A61K 31/133; A61K 31/663; A23L 1/30; A23L 2/52

See application file for complete search history.

(56) References Cited

U.S. PATENT DOCUMENTS

| | | |
|---|---|---|
| 7,504,497 B2 | 3/2009 | Douglass et al. |
| 2006/0205815 A1 | 9/2006 | Patel |
| 2010/0080863 A1 | 4/2010 | Sommerfeld et al. |
| 2012/0207822 A1 | 8/2012 | Hazen et al. |

FOREIGN PATENT DOCUMENTS

| | | |
|---|---|---|
| EP | 0155825 | 9/1985 |
| WO | 0110428 | 2/2001 |
| WO | 2011019685 | 2/2011 |
| WO | 2012109065 | 8/2012 |

OTHER PUBLICATIONS

Yamamoto et al. "N-Methylethanolamine attenuates cardiac fibrosis and improves diastolic function: inhibition of phospholipase D as a possible mechanism".*
Varughese et al. "Is Hypertension a Prothrombotic State?". Current Hypertension Reports, 2005, 7: 168-173.*
Al-Waiz et al. "The exogenous origin of trimethylamine in the mouse," Metabolism, 41: 135-136, 1992.
Al-Waiz et al. "The relative importance of N-oxidation and N-demethylation in the metabolism of trimethylamine in man," Toxicology, 43: 117-121, 1987.
Backhed et al. "The gut microbiota as an environmental factor that regulates fat storage," Proc Natl Acad Sci USA, 101:15718-15723, 2004.
Bain et al. "Trimethylamine: metabolic, pharmacokinetic and safety aspects," Curr Drug Metab, 6: 227-240; 2005.
Cannon et al. "Antibiotic treatment of *Chlamydia pneumoniae* after acute coronary syndrome," N Engl J Med, 352: 1646-1654, 2005.
De La Huerga et al. "Urinary excretion of choline metabolites following choline administration in normals and patients with hepatobiliary diseases," J Clin Invest, 30:463-470, 1951.
Dumas et al. "Metabolic profiling reveals a contribution of gut microbiota to fatty liver phenotype in insulin-resistant mice," Proc Natl Acad Sci USA, 103:12511-12516, 2006.
Erdmann et al. "On the Alleged occurrence of Trimethylamine in the urine," J Biol Chem, 8: 57-60, 1910.
Executive Summary of the Third Report of the National Cholesterol Program (NCEP) Expert Panel on Detection, Evaluation and Treatment of High Blood Cholesterol in Adults (Adult Treatment Panel III) JAMA, 285:2486-2497, 2001.
Gill et al. "Metagenomic analysis of the human distal gut microbiome," Science, 312:1355-1359, 2006.
Grayston et al. "Azithromycin for the secondary prevention of coronary events," N Engl J Med, 352:1637-1645, 2005.
Ihle et al. "Determination of body burden of uremic toxins," Clin Nephrol, 22: 82-89, 1984.
Kathiresan et al. "Polymorphisms associated with cholesterol and risk of cardiovascular events," N Engl J Med, 358:1240-1249, 2008.
Lang et al. "Isoform specificity of trimethylamine N-oxygenation by human flavin-containing monooxygenase (FMO) and P450 enzymes: selective catalysis by FMO3," Biochem Pharmacol, 56: 1005-1012, 1998.
Li et al. "Phosphatidylcholine and choline homeostasis," J Lipid Res, 49: 1187-1194, 2008.

(Continued)

*Primary Examiner* — Renee Claytor
(74) *Attorney, Agent, or Firm* — Casimir Jones S.C.

(57) ABSTRACT

Provided herein are compositions for the treatment and/or prevention of cardiovascular disease (CVD), and methods of application and use thereof. In particular, the present invention provides treatment and/or prevention of cardiovascular disease with compounds that inhibit the production of TMA in the gut, such as 3,3-dimethyl-1-butanol (DMB) or other compounds represented by Formula I or as shown in FIGS. 20-23.

12 Claims, 28 Drawing Sheets

(56) References Cited

OTHER PUBLICATIONS

Loscalzo "Lipid metabolism by gut microbes and atherosclerosis," Circ Res, 109: 127-129, 2011.
Martin et al. "Probiotic modulation of symbiotic gut microbial-host metabolic interactions in a humanized microbiome mouse model," Mol Syst Biol, 4: 157, 2008.
Patterson et al., USDA Database for the Choline Content of Common Foods, Release Two, 1-37, 2008.
Pimentel et al. "Rifaximin therapy for patients with irritable bowel syndrome without constipation," N Engl J Med, 364: 22-32, 2011.
Prentiss et al. "The metabolism of choline by the germfree rat," Arch Biochem Biophys, 94: 424-429, 1961.
Simenhoff et al. "Amine metabolism and the small bowel in uraemia," Lancet, 2:818-821, 1976.
Stella et al. "Susceptibility of human metabolic phenotypes to dietary modulation," J Proteome Res, 5: 2780-2788, 2006.
Vance, "Boehringer Mannheim Award lecture. Phosphatidylcholine metabolism: masochistic enzymology, metabolic regulation, and lipoprotein assembly," Biochem Cell Biol, 68: 1151-1165, 1990.
Wang et al. "Gut flora metabolism of phosphatidylcholine promotes cardiovascular disease," Nature, 472(7341)57-63, 2011.
Wen et al. "Innate immunity and intestinal microbiota in the development of Type 1 diabetes," Nature, 455: 1109-1113, 2008.
Yancey et al. "Trimethylamine oxide, betaine and other osmolytes in deep-sea animals: depth trends and effects on enzymes under hydrostatic pressure," Cell Mol Biol, 50: 371-376, 2004.
Zeisel et al. "Choline: critical role during fetal development and dietary requirements in adults," Annu Rev Nutr, 26:229-250, 2006.
Zhang et al. "Dietary precursors of trimethylamine in man: a pilot study," Food Chem Toxicol, 37: 515-520, 1999.
International Search Report and Written Opinion for PCT/US2013/045197, mailed Jan. 24, 2014, 17 pages.
Tracey, "Extra-Virgin Olive Oil Reduces Need for Blood Pressure Medication," WebMD, 2000, 2 pages.
Whittle et al., "Human Breath Odors and Their Use in Diagnosis," Ann. N.Y. Acad. Sci., 2007, 1098:252-266.
Cancernet, Deep and Superficial Vein Thrombosis, Mar. 25, 2009, Cancernet.co.uk via Waybachmachine.org, 1 page.
Starling, "Vigin Olive Oil Polypheonls Reduce Platelet Aggregation: Rat Study," Sep. 12, 2008, Nutraingredients.com, 2 pages.
MedicineNet, "Trimethylaminuria," Sep. 2, 2003, MedicineNet.com via Waybackmachine.org, 1 page.

* cited by examiner choline

Trimethylamine N-oxide
(TMAO)

3,3-dimethyl-1-butanol (DMB)

A.

B.

Choline Inhibitor Series

Betaine Inhibitor Series

Carnitine Inhibitor Series

GPC, PC and LPC Inhibitor Series

Choline 2,2-dimethyl-1-butanol (DMB)

2-Trimethylsilylethanol

P-Choline

Elemental analogues

Inhibitors Ester Series

Inhibitors Homologue Series

Inhibitors Phosphoester Series n = 0, 1, 2, 3, 4, 5, 6, 7,...etc.
R = H, Alkyl Group, etc.
Y = C, N, Si, P, S,...etc.

Inhibitors Homologue Ester Series

Inhibitors Homologue Thioester Series

Inhibitors Homologue Thionylester Series 5,5-dimethyl-3-hydroxyhexanoic Acid

4-Trimethylsilyl-3-hydroxybutyric Acid

P-Carnitine

Inhibitor Homologue Series

Inhibitor Homologue Ester Series

Inhibitor Homologue Thioester Series

Inhibitor Homologue Thionylester Series

Structural analogues of choline choline 3,3-dimethyl-1-butanol (DMB)

N,N-dimethylethanolamine (DMEA)

N-methylethanolamine (MEA)

ethanolamine (EA)

trimethylsilyl ethanol

P, P, P-trimethyl ethanolphosphine

Proteus mirabilis lysate cleavage of choline was inhibited by trimethylsilylethanol Reaction system contains 50 μM (choline + choline-d9) and 4.5 mg Proteus mirabilis protein lysate in 1.5 ml 10 mM Hepes, pH 7.4, 37 °C for 22 hours.

TREATMENT AND PREVENTION OF CARDIOVASCULAR DISEASE AND THROMBOSIS

CROSS-REFERENCE TO RELATED APPLICATIONS

The present application claims priority to U.S. Provisional Patent Application 61/658,208, filed Jun. 11, 2012, which is incorporated by reference in its entirety.

FIELD OF THE INVENTION

Provided herein are compositions for the treatment and/or prevention of cardiovascular disease (CVD), and methods of application and use thereof. In particular, the present invention provides treatment and/or prevention of cardiovascular disease with compounds that inhibit TMA productions in the gut, such as 3,3-dimethyl-1-butanol (DMB) or other compounds represented by Formula I or shown in the figures.

BACKGROUND

Cardiovascular disease (CVD) is the general term for heart and blood vessel diseases, including atherosclerosis, coronary heart disease, cerebrovascular disease, aorto-iliac disease, and peripheral vascular disease. Subjects with CVD may develop a number of complications, including, but not limited to, myocardial infarction, stroke, angina pectoris, transient ischemic attacks, congestive heart failure, aortic aneurysm and death. CVD accounts for one in every two deaths in the United States and is the number one killer disease. Thus, prevention of cardiovascular disease is an area of major public health importance.

A low-fat diet and exercise are recommended to prevent CVD. In addition, a number of therapeutic agents may be prescribed by medical professionals to those individuals who are known to be at risk having CVD. These include lipid-lowering agents that reduce blood levels of cholesterol and triglycerides, agents that normalize blood pressure, agents, such as aspirin, or platelet ADP receptor antagonists that prevent activation of platelets and decrease vascular inflammation (e.g., clopidogrel and ticlopidine), and pleiotrophic agents such as peroxisome proliferator activated receptor (PPAR) agonists, with broad-ranging metabolic effects that reduce inflammation, promote insulin sensitization, improve vascular function, and correct lipid abnormalities. More aggressive therapy, such as administration of multiple medications or surgical intervention may be used in those individuals who are at high risk of having CVD. Since CVD therapies may have adverse side effects, it is desirable to have methods for identifying those individuals who are at risk, particularly those individuals who are at high risk of experiencing an adverse cardiac event near term.

Major risk factors for cardiovascular disease include age, hypertension, family history of premature CVD, smoking, high total cholesterol, low HDL cholesterol, obesity and diabetes. The major risk factors for CVD are additive, and are typically used together by physicians in a risk prediction algorithm to target those individuals who are most likely to benefit from treatment for CVD. Testable markers of CVD include: level of aortic plaque formation, total blood cholesterol level, blood triglyceride level, blood low density lipoprotein levels, blood high density lipoprotein levels, formation of foam cells, and levels of choline-related trimethylamine (TMA) and trimethylamine-containing compounds, such as trimethylamine N-oxide (TMAO).

SUMMARY OF THE INVENTION

Provided herein are compositions for the treatment and/or prevention of cardiovascular disease (CVD), and methods of application and use thereof. In particular, the present invention provides treatment and/or prevention of cardiovascular disease with compounds that inhibit TMA productions in the gut, such as 3,3-dimethyl-1-butanol (DMB), N,N-dimethylethanolamine (DMEA), N-methylethanolamine (MEA), ethanolamine (EA), trimethylsilyl ethanol, and P,P,P-trimethyl ethanolphosphine; or other compounds represented by Formula I. Formula I is as follows:

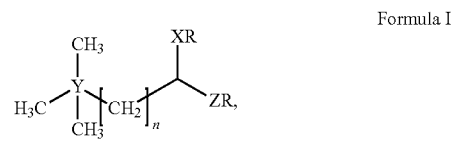

wherein n is an integer, or n is 0, indicating that $CH_2$ is not present;
wherein Y is C, Si, P, S, Ge, Sn, Pb, P, As, Sb, or Bi;
wherein X is O or S and the corresponding bond is either present or absent or double,
wherein R is H, an alkyl group, alkenyl group, alkynyl group, phenyl group, or a benzyl group;
wherein Z is C, $CH_2$, CH, O or S,
wherein XR is an ester, thioester, or thionester; glycerol, or one of the following three formulas:

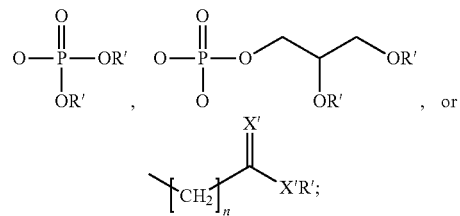

wherein R' is H, an alkyl group, alkenyl group, alkynyl group, phenyl group, or a benzyl group; and
wherein X' is O, or S.

In some embodiments, the present invention provides methods for the treatment and/or prevention of cardiovascular disease and/or thrombosis comprising: a) identifying a subject as having increased platelet aggregation and/or elevated TMAO levels, and b) administering to the subject a composition comprising N,N-dimethylethanolamine (DMEA), N-methylethanolamine (MEA), ethanolamine (EA), trimethylsilyl ethanol, and P,P,P-trimethyl ethanolphosphine, or a compound represented by Formula I (e.g., dimethylbutanol and/or a derivative thereof), and/or a gut targeting antibiotic and/or a prebiotic (e.g. a fiber containing food that alters intestinal flora composition) and/or a probiotic (e.g., probiotic containing food such as yogurt). In certain embodiments, the composition comprises dimethylbutanol or a compound shown in FIGS. 20-23. In further embodiments, the identifying comprises viewing results (e.g., on paper or on a computer screen) of a platelet aggregation assay performed on a sample from the subject which shows increased platelet aggregation. In further embodiments, the identifying comprises viewing results of a TMAO assay performed on a sample from the subject which show elevated TMAO levels. In certain embodiments, the identifying comprises viewing results of a TMA or TMAO assay performed on a sample or exhaled breath from said subject which show elevated TMA or TMAO levels.

In some embodiments, the composition comprises a compound of Formula I (or N,N-dimethylethanolamine (DMEA), N-methylethanolamine (MEA), ethanolamine (EA), trimethylsilyl ethanol, and P,P,P-trimethyl ethanolphosphine) containing food or beverage. In further embodiments, the composition comprises food or liquid containing a compound of Formula I (or N,N-dimethylethanolamine (DMEA), N-methylethanolamine (MEA), ethanolamine (EA), trimethylsilyl ethanol, and P,P,P-trimethyl ethanolphosphine) selected from the group consisting of but not limited to: olive oil, extra virgin olive oil, grape seed oil, yeast containing food, and red wine. In other embodiments, the composition comprises a compound beneficial for reducing TMAO levels. In certain embodiments, the composition is provided in a pill or capsule (e.g., with a filler or binder). In particular embodiments, the compound of Formula I (e.g., dimethylbutanol) prevent TMA formation from choline or other trimethylamine nutrients (e.g. carnitine, glycerophosphocholine, phosphocholine, phosphatodylcholine) from gut flora, or impairs choline transport. In additional embodiments, the compound of Formula I (or N,N-dimethylethanolamine (DMEA), N-methylethanolamine (MEA), ethanolamine (EA), trimethylsilyl ethanol, and P,P,P-trimethyl ethanolphosphine) induces one or more of the following when administered to a subject: reduced trimethyl amine level, reduce total cholesterol level, reduced LDL level, increased HDL level, and reduced triglyceride level. In further embodiments, the compound of Formula I reduces the risk of cardiovascular disease when administered to a subject. In other embodiments, the compound of Formula I (or N,N-dimethylethanolamine (DMEA), N-methylethanolamine (MEA), ethanolamine (EA), trimethylsilyl ethanol, and P,P,P-trimethyl ethanolphosphine) reduces the risk of platelet activation and/or thrombosis when administered to a subject.

In some embodiments, the present invention provides methods of treating and/or preventing cardiovascular disease and/or thrombosis comprising administering to a subject a composition comprising a compound of Formula I (e.g., dimethylbutanol and/or derivatives thereof and/or a compound shown in FIGS. 20-23, such as N,N-dimethylethanolamine (DMEA), N-methylethanolamine (MEA), ethanolamine (EA), trimethylsilyl ethanol, and P,P,P-trimethyl ethanolphosphine). In further embodiments, the subject has been determined to have increased platelet aggregation. In certain embodiments, the subject has been determined to have an elevated TMAO level. In further embodiments, the administering is under such conditions that at least one symptom of the cardiovascular disease and/or the thrombosis is reduced or eliminated. In further embodiments, the subject has a diet high in choline. In other embodiments, the composition comprises dimethylbutanol. In certain embodiments, the administration of the composition inhibits the conversion of choline to trimethyl amines. In other embodiments, the administration of the composition inhibits choline transport.

In some embodiments, Formula I has a formula selected from the group consisting of:

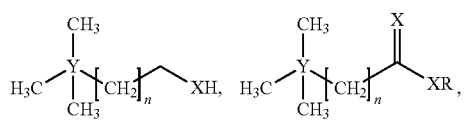

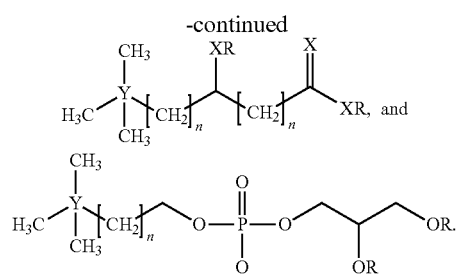

In other embodiments, Formula I has a formula selected from the group consisting of:

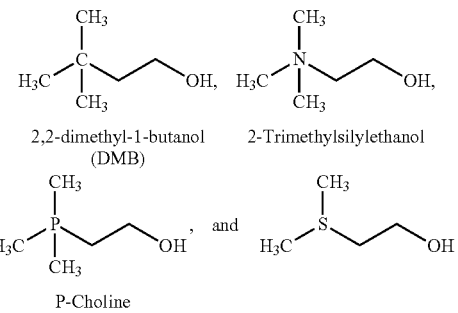

2,2-dimethyl-1-butanol (DMB)  2-Trimethylsilylethanol

P-Choline

In certain embodiments, Formula I has a formula selected from the group consisting of:

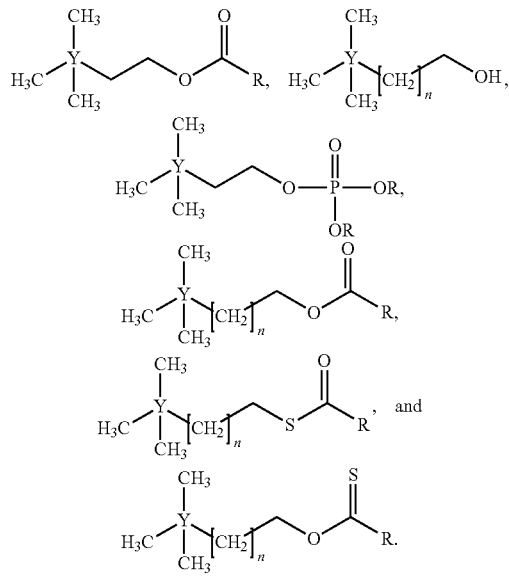

In some embodiments, Formula I has a formula selected from the group consisting of:

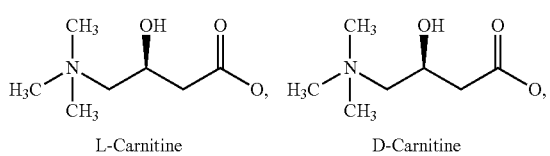

L-Carnitine  D-Carnitine

-continued

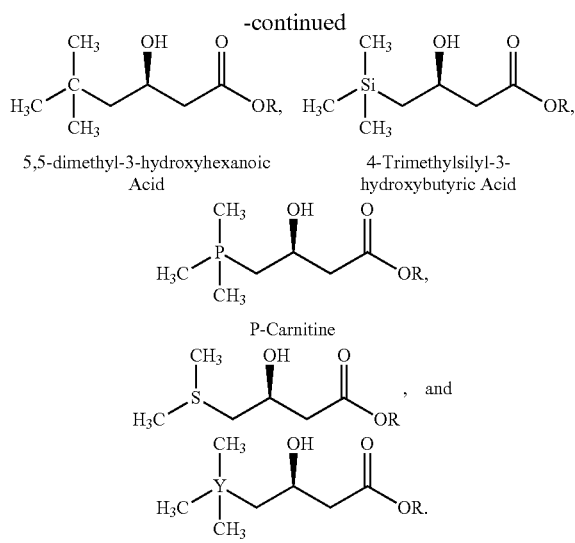

In further embodiments, Formula I has a formula selected from the group consisting of:

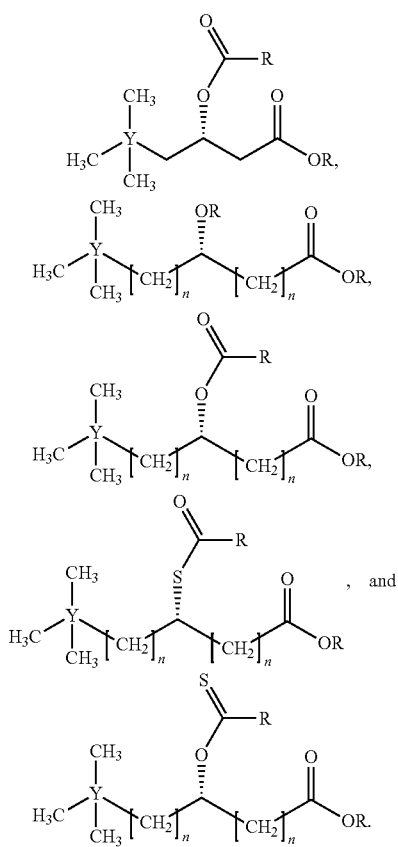

In particular embodiments, the composition is co-administered with one or more agents which provide therapy for cardiovascular disease. In further embodiments, the one or more agents comprises one or more antibiotics that target gut flora (e.g., antibiotics that kill bacteria in the gut that are responsible for generating TMAO). In further embodiments, the composition is co-administered with one or more agents which provide therapy for inflammatory disease. In further embodiments, the composition is co-administered with one or more agents that reduces TMA and/or TMA levels, or improves intestinal motility (e.g. fiber, psyllium or some other prebiotic).

In some embodiments, the present invention provides methods of preventing thrombosis, heart-attack, and/or reducing platelet hyper-responsiveness in a subject undergoing a procedure comprising: administering a gut flora targeting antibiotic to a subject prior to a procedure, wherein the procedure is associated with a risk of causing thrombosis, heart-attack, and/or platelet hyper-responsiveness, and wherein the administering is under conditions such that the thrombosis and/or the heart attack is prevented, and/or the platelet hyper-responsiveness is reduced.

In certain embodiments, the procedure is an instrumented procedure selected from the group consisting of: dental, surgical, colonoscopy, and cardiovascular stenting procedure. In certain embodiments, the gut flora targeting antibiotic is selected from the group consisting of: ciprofloxin, flagyl (metronidazole), vancomycin, neomycin sulfate, and ampicillin. In particular embodiments, the administering is within 50 hours of the procedure (e.g., 48 hours . . . 40 hours . . . 36 hours . . . 28 hours . . . 22 hours . . . 15 hours . . . 10 hours . . . 7 hours . . . 5 hours . . . 4 hours . . . 3 hours . . . 2 hours . . . 1 hour . . . 5 minutes of the procedure). In further embodiments, the methods further comprise, prior to the procedure, viewing results of a platelet aggregation assay on a sample taken from the subject after the administering the gut flora targeting antibiotic. In additional embodiments, the methods further comprise performing the procedure.

In some embodiments, the present invention provides methods comprising: a) performing a platelet aggregation assay on a sample from a subject to determine if said sample shows elevated platelet aggregation compared to normal levels; and b) recommending, and/or generating a reports that recommends, that said subject receive a therapeutic composition for treating cardiovascular disease or thrombosis, wherein said therapeutic composition comprises a compound of Formula I (e.g., dimethylbutanol and/or a derivative thereof) and/or a gut targeting antibiotic, prebiotic and/or a probiotic.

In certain embodiments, the present invention provides methods comprising: a) performing a TMAO level assay on a sample from a subject to determine if said sample shows elevated TMAO levels compared to normal levels; and b) recommending, or generating a reports that recommends, that said subject receive a therapeutic composition for treating cardiovascular disease or thrombosis, wherein said therapeutic composition comprises a compound of Formula I (e.g., dimethylbutanol and/or a derivative thereof) and/or a gut targeting antibiotic, prebiotic and/or a probiotic.

In certain embodiments, the present invention provides methods comprising: a) performing a TMA level assay on a sample or exhaled breath from a subject to determine if said sample or exhaled breath shows elevated TMA levels compared to normal levels; and b) recommending, or generating a reports that recommends, that said subject receive a therapeutic composition for treating cardiovascular disease or thrombosis, wherein said therapeutic composition comprises a compound of Formula I (e.g., dimethylbutanol and/or a derivative thereof) and/or a gut targeting antibiotic, prebiotic and/or a probiotic.

In some embodiments, the present invention provides a composition for the treatment and/or prevention of cardiovascular disease comprising a compound of Formula I (e.g., dimethylbutanol, derivatives thereof, or related compounds) configured for administration to a subject. In some embodiments, the composition comprises dimethylbutanol. In some embodiments, compositions further comprise one or more pharmaceutical agents that provide therapy for cardiovascular disease. In some embodiments, compositions further comprise one or more pharmaceutical carriers. In some embodiments, the compound of Formula I impairs choline transport. In some embodiments, the compound of Formula I induces one or more of the following when administered to a subject: reduced trimethyl amine level, reduce total cholesterol level, reduced LDL level, increased HDL level, and reduced triglyceride level. In some embodiments, the compound of Formula I reduces the risk of cardiovascular disease when administered to a subject. In some embodiments, the compound of Formula I reduces the risk of inflammatory disease when administered to a subject. In some embodiments, the composition is formulated with a physiologically acceptable buffer. In some embodiments, the composition is provided in a pill or capsule with a filler or binder.

In some embodiments, the present invention provides a method of treating and/or preventing cardiovascular disease comprising administering to a subject a composition comprising a compound of Formula I (e.g., dimethylbutanol, derivatives thereof, or related compounds). In some embodiments, the subject is at risk of developing cardiovascular disease. In some embodiments, the subject suffers from cardiovascular disease. In some embodiments, administering is under such conditions that at least one symptom of said cardiovascular disease is reduced or eliminated. In some embodiments, the subject has a diet high in choline. In some embodiments, the composition comprises dimethylbutanol. In some embodiments, the composition inhibits the conversion of choline to TMA or other trimethyl amines. In some embodiments, administration of the composition inhibits choline transport. In some embodiments, the composition comprising a compound of Formula I is co-administered with one or more agents that provide therapy for cardiovascular disease. In some embodiments, the composition is co-administered with one or more agents that provide therapy for inflammatory disease.

In some embodiments, the present invention provides a method of treating, preventing, or ameliorating signs or symptoms of cardiovascular disease in a subject. In some embodiments, the compound of Formula I (e.g., dimethylbutanol, derivatives thereof, or related compounds), or N,N-dimethylethanolamine (DMEA), N-methylethanolamine (MEA), ethanolamine (EA), trimethylsilyl ethanol, and P,P,P-trimethyl ethanolphosphine, which is provided in a kit with one or more other therapeutics, nutriceuticals, supplements, pharmaceuticals, and/or foods. In some embodiments, the compound of Formula I is (e.g., dimethylbutanol, derivatives thereof, or related compounds) is provided as a food or drink supplement. In some embodiments, the compound of Formula I or those in FIGS. 20-23 is (e.g., dimethylbutanol, derivatives thereof, or related compounds) is provided as a pharmaceutical. In some embodiments, the compound of Formula I (e.g., dimethylbutanol, derivatives thereof, or related compounds) is provided as a part of a comprehensive CVD treatment or prevention strategy and/or in conjunction with other therapies, healthy diet, exercise, and/or other strategies known to clinicians and those in the field.

In some embodiments, administration of a compound of Formula I or those shown in FIGS. 20-23 (e.g., DMB, a compound comprising DMB, a DMB-related compound, and/or derivatives thereof) provides therapy (e.g. palliative, preventative, therapeutic, etc.) for one or more cardiovascular diseases including, but not limited to: angina, arrhythmia, atherosclerosis, cardiomyopathy, congestive heart failure, coronary artery disease (CAD), carotid artery disease, endocarditis, heart attack (e.g. coronary thrombosis, myocardial infarction [MI]), high blood pressure/hypertension, hypercholesterolemia/hyperlipidemia, mitral valve prolapsed, peripheral artery disease (PAD), stroke, etc.

BRIEF DESCRIPTION OF THE DRAWINGS

FIG. 2A shows the difference in cholesterol accumulated in macrophages among structurally similar chemical compounds, choline, TMAO and dimethylbutanol (DMB). Male C57BL/6J.Apoe−/− mice (15 week old) were placed on normal chow (control) alone or supplemented in the presence of either choline (1.0%), TMAO (0.12%), or DMB (1.0%). Peritoneal macrophages were recovered from the indicated number of mice at 20 weeks of age and cellular cholesterol content was quantified by stable isotope dilution GC/MS, and normalized to DNA content. FIG. 2B shows the schematic illustration of overall pathway.

FIG. 9 also shows that DMB inhibits TMA and TMAO formation in the mice on a high choline diet.

FIG. 12 plots maximum amplitude of platelet aggregation responses versus the indicated diets and treatments (DMB or antibiotic suppression of flora). FIG. 12 shows that addition of DMB blocks platelet hyper-responsiveness (aggregation) from a high choline diet or endogenous TMAO.

FIG. 15 shows that DMB and antibiotics both block the reduction in in vivo thrombosis rates seen on a high choline diet and also block diet induced elevation TMAO levels.

DEFINITIONS

Figure 1:
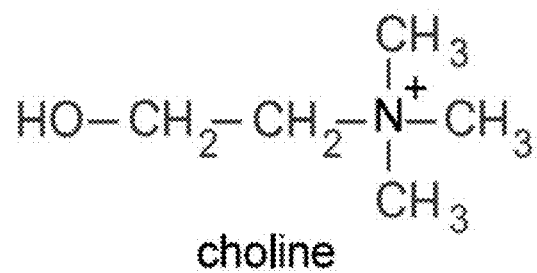
FIG. 1 shows molecular formulas of choline, trimethylamine N-oxide and 3,3-dimethyl-1-butanol (DMB).
Figure 1:
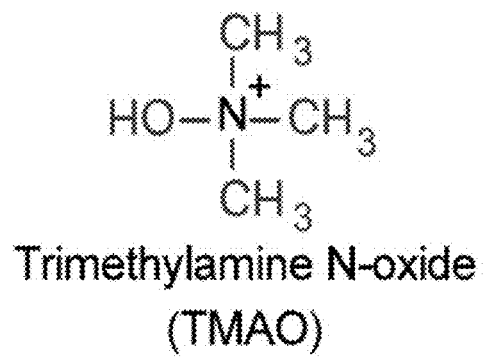
Figure 1:
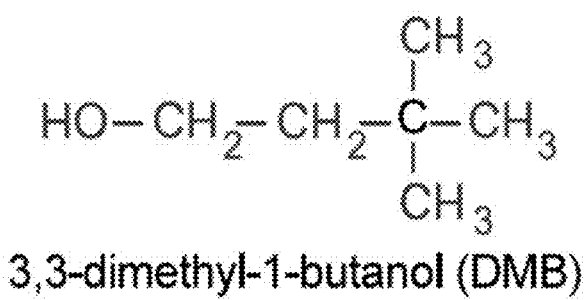

As used herein, the terms "cardiovascular disease" (CVD) or "cardiovascular disorder" are terms used to classify numerous conditions affecting the heart, heart valves, and vasculature (e.g., arteries and veins) of the body and encompasses diseases and conditions including, but not limited to arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (CAD), peripheral artery disease (PAD), and cerebrovascular disease.

As used herein, the term "atherosclerotic cardiovascular disease" or "disorder" refers to a subset of cardiovascular disease that include atherosclerosis as a component or precursor to the particular type of cardiovascular disease and includes, without limitation, CAD, PAD, cerebrovascular disease. Atherosclerosis is a chronic inflammatory response that occurs in the walls of arterial blood vessels. It involves the formation of atheromatous plaques that can lead to narrowing ("stenosis") of the artery, and can eventually lead to partial or complete closure of the arterial opening and/or plaque ruptures. Thus atherosclerotic diseases or disorders include the consequences of atheromatous plaque formation and rupture including, without limitation, stenosis or narrowing of arteries, heart failure, aneurysm formation including aortic aneurysm, aortic dissection, and ischemic events such as myocardial infarction and stroke A cardiovascular event, as used herein, refers to the manifestation of an adverse condition in a subject brought on by cardiovascular disease, such as sudden cardiac death or acute coronary syndromes including, but not limited to, myocardial infarction, unstable angina, aneurysm, or stroke. The term "cardiovascular event" can be used interchangeably herein with the term cardiovascular complication. While a cardiovascular event can be an acute condition, it can also represent the worsening of a previously detected condition to a point where it represents a significant threat to the health of the subject, such as the enlargement of a previously known aneurysm or the increase of hypertension to life threatening levels.

As used herein, the term "diagnosis" can encompass determining the nature of disease in a subject, as well as determining the severity and probable outcome of disease or episode of disease and/or prospect of recovery (prognosis). "Diagnosis" can also encompass diagnosis in the context of rational therapy, in which the diagnosis guides therapy, including initial selection of therapy, modification of therapy (e.g., adjustment of dose and/or dosage regimen or lifestyle change recommendations), and the like.

The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some embodiments, the subject is specifically a human subject.

DETAILED DESCRIPTION OF THE INVENTION

The present invention provides compositions and methods for treating subjects at risk of developing or having cardiovascular disease. In certain embodiments, a compound from Formula I is used to treat a subject at risk or developing or having cardiovascular disease. In some embodiments, 3,3,-Dimethyl-1-butanol (a.k.a. dimethylbutanol, DMB), an analog of choline in which the nitrogen atom of choline is replaced with a carbon (SEE FIG. 1), is administered to subjects. In some embodiments, the present invention provides administering a compound from Formula I or those shown in FIGS. 20-23 (e.g., DMB) to a subject at risk of developing or having cardiovascular disease. In some embodiments, a therapeutically effective amount of: a compound from Formula I or FIGS. 20-23 (e.g., DMB, a compound comprising DMB, a DMB-related compound, and/or derivatives thereof) is administered to a subject to treat and/or prevent CVD. In some embodiments, a compound of Formula I or in FIGS. 20-23 (e.g., DMB, a compound comprising DMB, a DMB-related compound, and/or derivatives thereof)

is co-administered to a subject in conjunction with one or more accepted treatments for CVD. In certain embodiments, a gut flora targeting antibiotic is administered to a subject to treat or prevent CVD and/or thrombosis.

Although the present invention is not limited to any particular mechanism of action and an understanding of the mechanism of action is not necessary to practice the present invention, when administered to a subject (e.g. human subject, animal test subject) a compound from Formula I (or N,N-dimethylethanolamine (DMEA), N-methylethanolamine (MEA), ethanolamine (EA), trimethylsilyl ethanol, and P,P,P-trimethyl ethanolphosphine) serves as a prebiotic that impairs choline transport, and thus, is able to lower trimethyl amine (e.g. TMAO) levels in plasma. In some embodiments, a compound from Formula I or FIGS. 20-23 administration results in reduced TMA levels. In some embodiments, a compound from Formula I administration results in reduced TMAO levels. In some embodiments, administering a compound from Formula I (or FIGS. 20-23) treats and/or prevents conditions and/or diseases where trimethyl amines (e.g. TMAO) are associated or causative (e.g. CVD, inflammatory diseases (e.g. rheumatoid arthritis)). Trimethyl amines are increased in inflammatory conditions and modulate macrophage activity from quiescent to active phenotypes. In some embodiments, a compound of Formula I is administered as a therapeutic for inflammatory diseases (e.g. CVD, rheumatoid arthritis, etc.).

In some embodiments, administration of a compound of Formula I, a compound comprising DMB, a DMB-related compound, and/or derivatives thereof, or N,N-dimethylethanolamine (DMEA), N-methylethanolamine (MEA), ethanolamine (EA), trimethylsilyl ethanol, and P,P,P-trimethyl ethanolphosphine, to a subject at risk of CVD, suspected of having CVD, or suffering from CVD results in improvement in one or more markers and risk factors for CVD (e.g. total cholesterol, LDL, HDL, triglycerides, TMAO, etc.). In some embodiments, administration of a compound of Formula I, DMB, a compound comprising DMB, a DMB-related compound, and/or derivatives thereof, or N,N-dimethylethanolamine (DMEA), N-methylethanolamine (MEA), ethanolamine (EA), trimethylsilyl ethanol, and P,P,P-trimethyl ethanolphosphine, to a subject at risk of CVD, suspected of having CVD, or suffering from CVD results in one or more of: a reduction in aortic plaque formation, a reduction in total cholesterol, a reduction in triglyceride levels in blood, a reduction in LDL levels in blood, an increase in HDL levels in blood, a reduction in the production and/or number of foam cells, a reduction in TMA (e.g. TMAO) generation (e.g. from choline), a reduction in microflora catalyzed TMA (e.g. TMAO) generation, and alterations in other indicators and/or risk factors of CVD.

In some embodiments, administration of a compound of Formula I, DMB, a compound comprising DMB, a DMB-related compound, or FIGS. 20-23, and/or derivatives thereof provides therapy (e.g. palliative, preventative, therapeutic, etc.) for one or more inflammatory diseases including, but not limited to: Alzheimer's disease, arthritis (e.g. rheumatoid arthritis), asthma, CVD (e.g. atherosclerosis), Crohn's disease, colitis, dermatitis, diverticulitis, hepatitis, irritable bowel syndrome (IBS), lupus erythematous, nephritis, Parkinson's disease, ulcerative colitis, etc. In some embodiments, administration of a compound of Formula I, as shown in FIGS. 20-23, DMB, a compound comprising DMB, a DMB-related compound, and/or derivatives thereof provides therapy (e.g. palliative, preventative, therapeutic, etc.) for one or more cardiovascular diseases including, but not limited to: angina, arrhythmia, atherosclerosis, cardiomyopathy, congestive heart failure, coronary artery disease (CAD), carotid artery disease, endocarditis, heart attack (e.g. coronary thrombosis, myocardial infarction (MI)), high blood pressure/hypertension, hypercholesterolemia/hyperlipidemia, mitral valve prolapsed, peripheral artery disease (PAD), stroke, etc.

In some embodiments, a compound of Formula I (e.g., DMB) or as shown in FIG. 20-23, provides therapy (e.g. palliative, preventative, therapeutic, etc.) for cardiovascular diseases and/or inflammatory diseases in which excess choline (e.g. excess dietary choline) is associated (e.g. causative). In some embodiments, a compound of Formula I (e.g., DMB) provides therapy (e.g. palliative, preventative, therapeutic, etc.) for diseases, conditions, and/or disorders in which excess trimethyl amine (e.g. TMAO, choline-derived TMA, etc.) is associated (e.g. causative). In some embodiments, DMB provides therapy (e.g. palliative, preventative, therapeutic, etc.) for diseases, conditions, and/or disorders in which trimethyl amine (e.g. TMAO, choline-derived TMA, etc.) is associated (e.g. causative). In some embodiments, a compound of Formula I (e.g., DMB) provides therapy (e.g. palliative, preventative, therapeutic, etc.) for diseases, conditions, and/or disorders in which excess trimethyl amine (e.g. TMAO, choline-derived TMA, etc.) is associated (e.g. causative). In some embodiments, compounds of Formula I (e.g., DMB-related compounds, and/or derivatives thereof) that inhibit the conversion of choline to TMA (e.g. TMAO) provide therapy for disease. In some embodiments, the compounds of Formula I (e.g., DMB-related compounds, and/or derivatives thereof) that inhibit choline transport provide therapy for disease. In some embodiments, compounds of Formula I (e.g, DMB-related compounds, and/or derivatives thereof) reduce the risk of CVD and/or other inflammatory diseases by any mechanism.

In some embodiments of the present invention, compositions are administered to a patient alone or in combination with other therapies, pharmaceuticals, supplements, and/or a specified diet, or in pharmaceutical compositions where it is mixed with excipient(s) or other pharmaceutically acceptable carriers. Depending on the goal of administration (e.g. severity of condition, duration of treatment, etc.), compositions (e.g., comprising a compound of Formula I, such as DMB) may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. In some embodiments, a compound of Formula I (e.g., DMB) may be administered in the form of a solid, semi-solid or liquid dosage form: such as tablet, capsule, pill, powder, suppository, solution, elixir, syrup, suspension, cream, lozenge, paste and spray formulated appropriately to provide the desired therapeutic profile. As those skilled in the art would recognize, depending on the chosen route of administration, the composition form is selected.

In some embodiments, a pharmaceutical composition (e.g., comprising a compound of Formula I, such as DMB) or N,N-dimethylethanolamine (DMEA), N-methylethanolamine (MEA), ethanolamine (EA), trimethylsilyl ethanol, and P,P,P-trimethyl ethanolphosphine, is administered in single or multiple doses. In some embodiments, a pharmaceutical composition (e.g., comprising a compound of Formula I, such as DMB, or those shown in FIGS. 20-23) is administered in a single dose. In some embodiments, a single oral pill or capsule is provided containing a pharmaceutical composition (e.g., comprising a compound of Formula I, such as DMB) is and one or more additional pharmaceutical agents. In some embodiments, a capsule is used containing a pharmaceutical composition (e.g., comprising a compound of Formula I, such as DMB, or as shown in FIGS. 20-23) in a form that release (e.g. immediate release, timed release, delayed release, etc.). The particular route of administration and the dosage regimen will be determined by one of skill, in keeping with the condition of the individual to be treated and said individual's response to the treatment. In some embodiments, substituents of a composition of the present invention may be adjusted to provide desirable solubility or other characteristics for administration by any suitable technique.

Figure 2A:
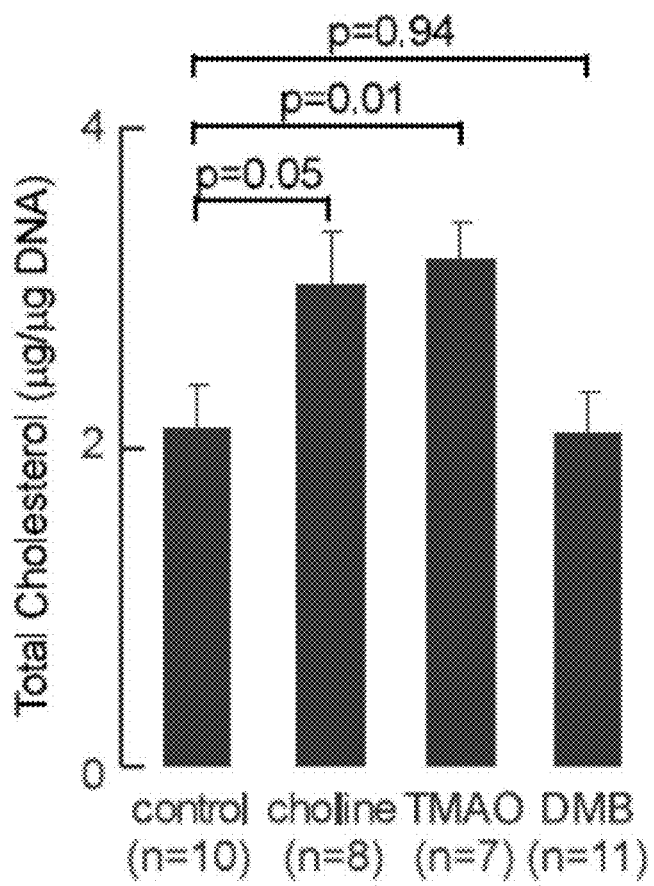
FIGS. 2A and 2B show the effects of structurally similar chemical compounds on macrophage cholesterol accumulation, and summary of overall pathway linking gut flora dependent metabolism of dietary PC and choline to atherosclerosis.
Figure 2B:
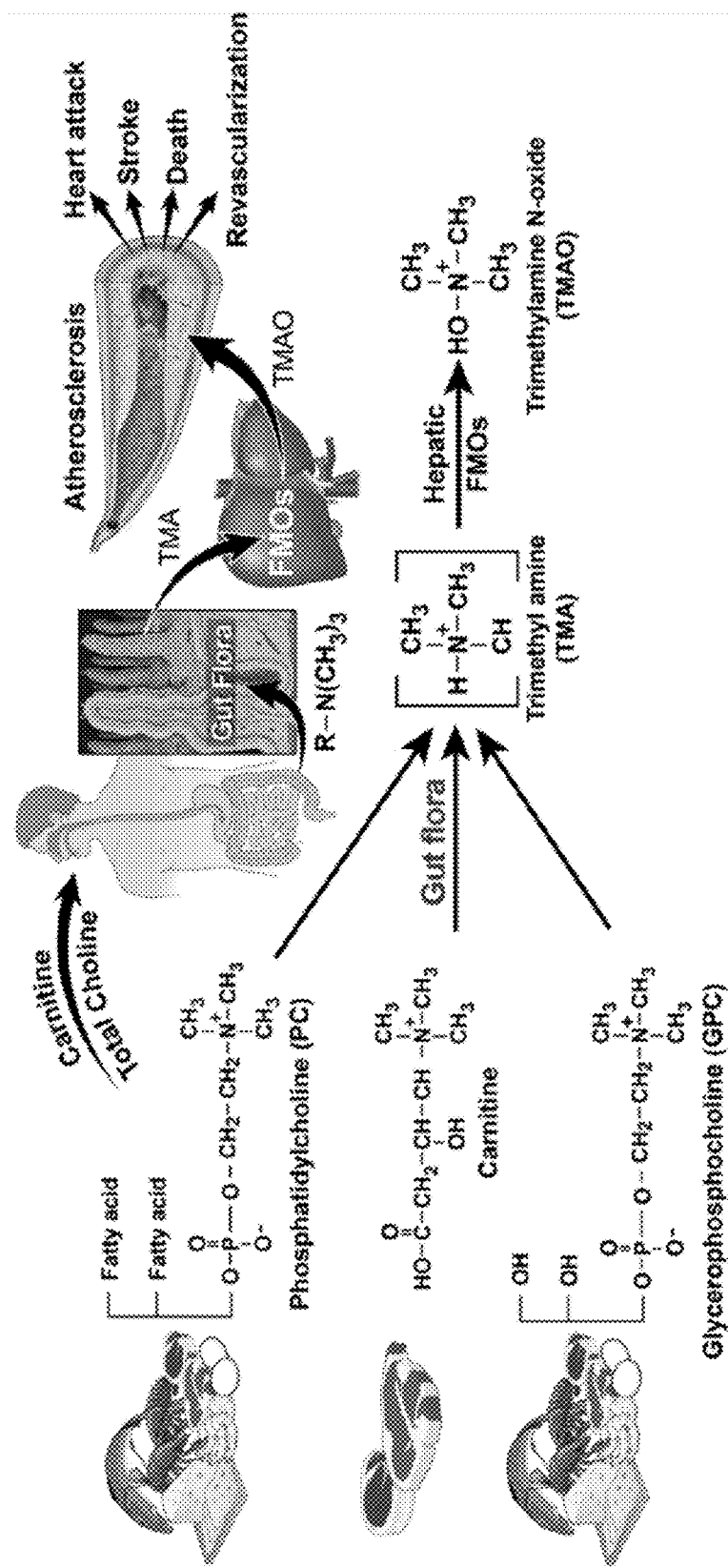

DMB is structurally similar to choline, except DMB lacks a C—N bond due to the substitution of a carbon atom for a nitrogen atom (SEE FIGS. 2A and 2B). As such, the present invention contemplates the use of choline derivatives (See, e.g., EP0155825 and US 2006020585; herein incorporated by reference in their entireties), modified such that they lack a C—N bond due to a similar nitrogen to carbon substitution. Exemplary compositions are presented in Formula I.

In certain embodiments, platelet aggregation tests are employed (e.g., to determine if a patient's platelets are hyper-responsive leading to an increased risk of CVD or thrombosis). Platelet aggregation or function tests are a group of assays that use equipment to measure the ability of platelets to aggregate and promote clotting in a sample of blood. There are a variety of tests available that are used to measure platelet function, as described below.

One type of assay is called a closure time assay. In this assay, blood is exposed to various substances that activate platelets. The blood is then drawn through a simulated wound, a small hole in a small tube that is coated with collagen, a protein that promotes platelet binding to wounds. In normal blood, activated platelets will bind to the coated hole, eventually plugging it. The time required to plug the hole is measured, which is called the closure time. The longer the closure time, the lower the platelet function. This test may be abnormal if the platelet count is low, if platelet function is reduced, if other proteins needed for platelet function are reduced or if anti-platelet medications are present.

Another type of assay is called a viscoelastometry assay. This type of assay is designed to determine the strength of a blood clot as it forms. Substances are added to blood to start clotting while clot strength is being measured over time. Measurements are made of total clot strength, time to reach maximum strength, and loss of strength over time. These tests may be abnormal if the platelet count is low, if platelet function is reduced, or if anti-platelet medications are present.

Another type of assay is an endpoint bead or endpoint platelet aggregation assay. These assays determine the number of coated beads or platelets that aggregate after substances are added to activate platelets. They provide a single measure of aggregation (an endpoint) rather than a measure of aggregation over time. More platelets aggregating or sticking to beads indicates better platelet function. These tests may be abnormal if the platelet count is low, if platelet function is reduced, or if anti-platelet medications are present.

Another type of assay is called a bleeding time assay. In the past, the primary screen for platelet dysfunction was the bleeding time—a test that involved making two small, shallow, standardized cuts on the inner forearm and measuring the amount of time that they took to stop bleeding.

Another type of assay is a platelet aggregometry assay. Many different substances can activate a platelet, including proteins in the wound, factors released from other activated platelets, and factors produced by the coagulation system that aids platelets in forming a strong plug to stop bleeding. Many different platelet abnormalities have been described due to problems with one or more of these activating systems. Platelet aggregometry is generally composed of 4 to 8 separate tests. In each test, a different platelet activating substance is added to blood, followed by measurement of platelet aggregation over several minutes. When complete, a physician or technician reviews and interprets the entire panel of tests to determine if there is any evidence of abnormal platelet function.

An additional assay is based on flow cytometry. Platelets can be evaluated for functional defects using flow cytometry. This test uses lasers to determine proteins that are present on the platelet surface and how they change when the platelet is activated.

An additional assay is based on in vivo thrombosis rates. The activation of platelets within the living organism can be evaluated in response to a specific stimuli and monitored, such as with vital microscopy that directly images blood flow and a growing thrombus (platelet clot) within the vessel in real time.

In certain embodiments, antibiotics (e.g., gut flora targeting antibiotics) are used in the methods of the present invention. The present invention is not limited by the type of antibiotics employed. Examples of such antibiotic agents include, but are not limited to, aminoglycosides, Ansamycins, Carbacephems, Carbapenems, Cephalosporins, Glycopeptides, Macrolides, Monobactams, Penicillins, Polypeptides, Polymyxin, Quinolones, Sulfonamides, Tetracyclines, and others (e.g., Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in US), Thiamphenicol, Timidazole, Dapsone, and lofazimine). Examples of these classes of antibiotics include, but are not limited to, Amikacin, Gentamicin, Kanamycin, Neomycin, Netilmicin, Streptomycin, Tobramycin, Paromomycin, Geldanamycin, Herbimycin, Loracarbef, Ertapenem, Doripenem, Imipenem/Cilastatin, Meropenem, Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Azithromycin, Clarithromycin, Dirithromycin, Erythromycin, Roxithromycin, Troleandomycin, Telithromycin, Spectinomycin, Aztreonam, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Bacitracin, Colistin, Polymyxin B, Ciprofloxacin, Enoxacin, Gatifloxacin, Levofloxacin, Lomefloxacin, Moxifloxacin, Norfloxacin, Ofloxacin, Trovafloxacin, Grepafloxacin, Sparfloxacin, Temafloxacin, Mafenide, Sulfonamidochrysoidine (archaic), Sulfacetamide, Sulfadiazine, Sulfamethizole, Sulfanilimide (archaic), Sulfasalazine, Sulfisoxazole, Trimethoprim, rimethoprim-Sulfamethoxazole (Co-trimoxazole) (TMP-SMX), Demeclocycline, Doxycycline, Minocycline, Oxytetracycline, and Tetracycline.

EXPERIMENTAL

Example 1

Structural Specificity of Phaophatidylcholine Metabolites

Experiments were conducted during development of embodiments of the present invention to examine the structural specificity of phaophatidylcholine metabolites in promoting a pro-atherogenic macrophage phenotype as monitored by endogenous foam cell formation. C57BL/6J.Apoe−/− mice at time of weaning were placed on either normal chow diet (control) or normal chow supplemented with either choline, TMAO or the choline analog DMB, where the quaternary amine nitrogen of choline is replaced with a carbon (SEE FIG. 2, right). Thus, DMB is structurally identical to choline except there is no C—N bond for potential cleavage and TMA formation by gut flora. Mice fed diets supplemented with either trimethylamine species (choline or TMAO) showed both increased macrophage cholesterol content and elevated plasma levels of TMAO. In contrast, dietary DMB supplementation resulted in no TMAO increase, and no increased accumulation of cholesterol in endogenous macrophages.

Example 2

Effect of DMB on Atherosclerosis

Figure 3:
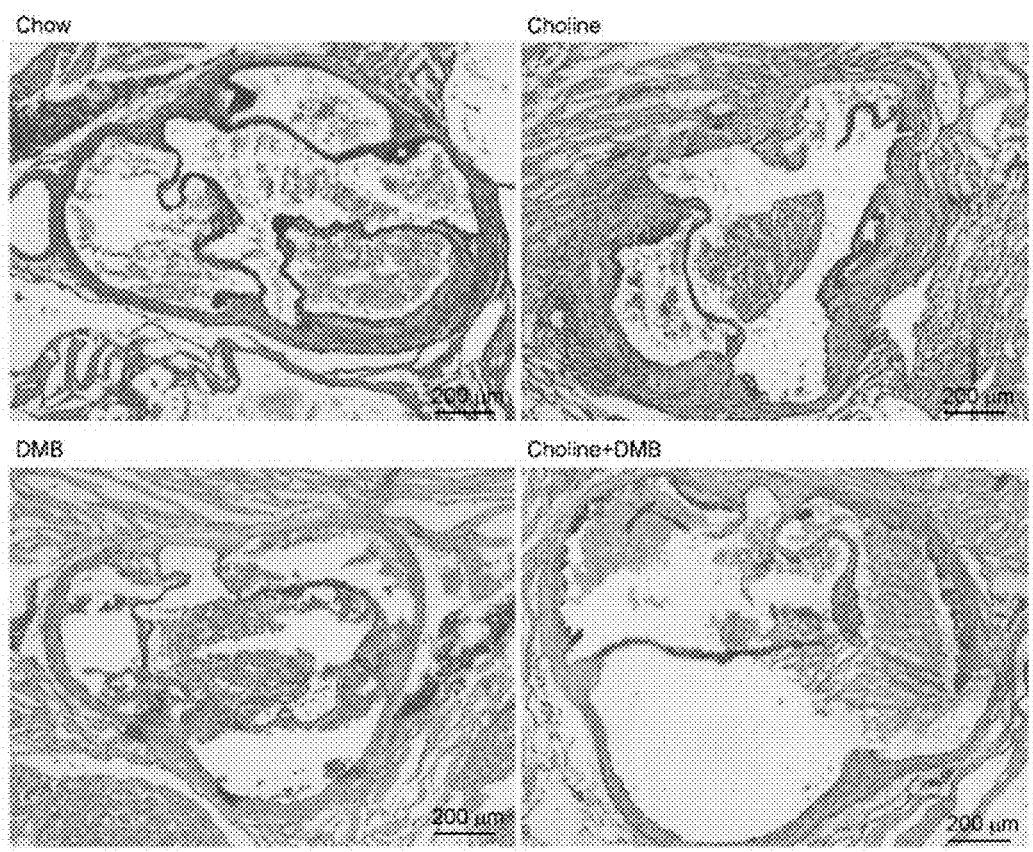
FIG. 3 shows images of aortic root sections demonstrating the effect of diet on the accumulation of aortic lesions.

Experiments were conducted during development of embodiments of the present invention which demonstrate that a diet high in choline (e.g. a Western diet) results in enhanced atherosclerosis, and addition of the compound DMB blocks the diet-induced enhanced artherosclerosis. C57BL/6J.Apoe−/− male mice at the time of weaning (4 weeks) were placed on chow diet supplemented with 1.3% choline, 1.3% DMB, both, or neither. Aortic root section was stained with oil red O/hematoxin. The red oil staining area inside the aorta indicates lesion plaque (SEE FIGS. 3 and 4). The addition of DMB to normal chow diet significantly (~90%) reduced aortic plaque formation in the apoE−/− mice (SEE FIG. 4). Further, addition of choline completely blocked the increases in atherosclerotic plaque induced by the high choline diet (SEE FIG. 4). These data indicate DMB is capable of reducing aortic plaque formation and reversing plaque formation induced by a high choline diet. These data further indicate that DMA may provide therapy for prevention and/or treatment of plaque formation and atherosclerotic heart disease.

Example 3

Effect of DMB on Lipoprotein Profile

Figure 5:
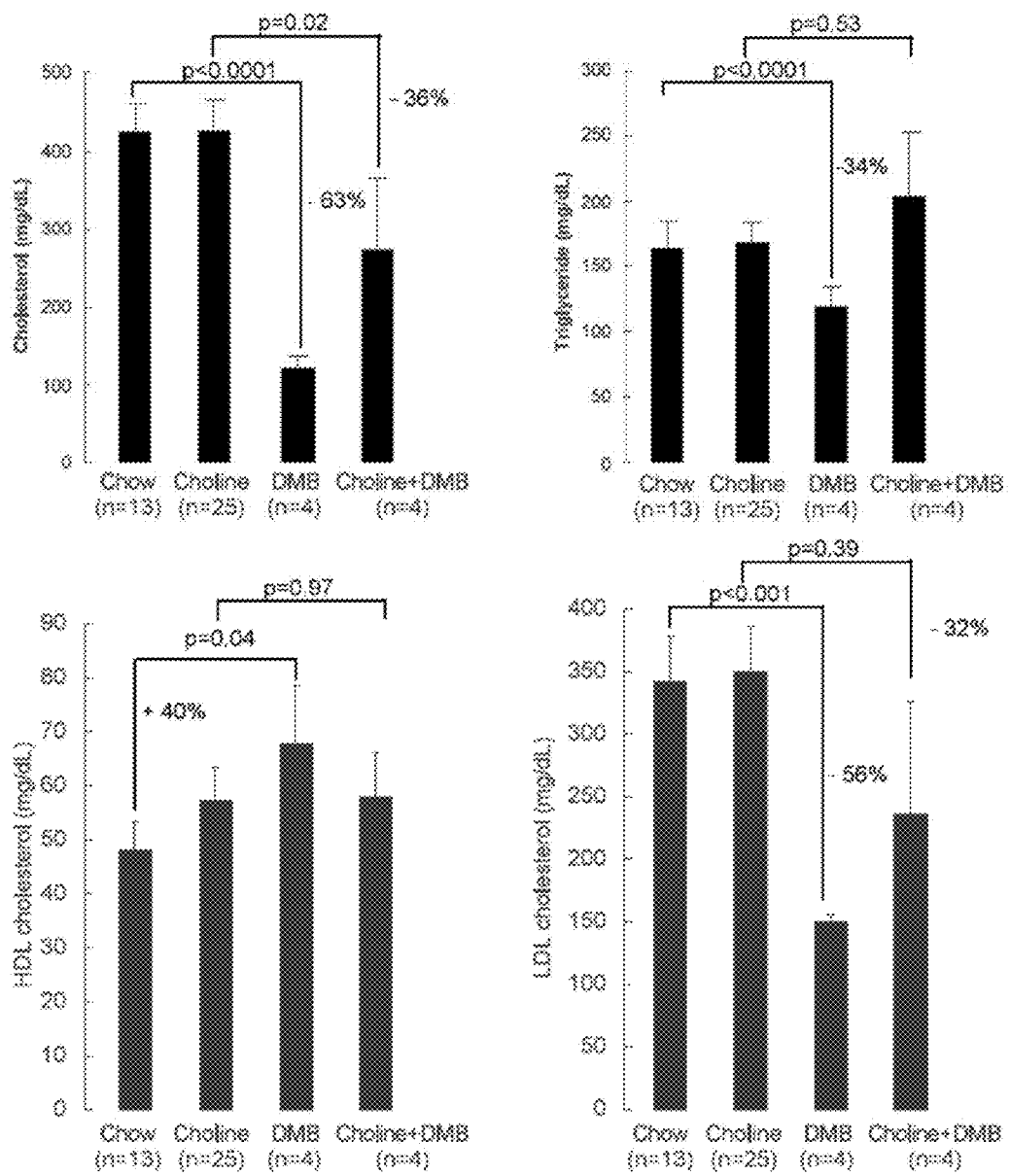
FIG. 5 shows plots of plasma levels of cholesterol, triglyceride, LDL-cholesterol, and HDL-cholesterol, and how administration of DMB can reduce atherogenic lipid levels

Experiments were conducted during development of embodiments of the present invention to compare plasma levels of (1) cholesterol, (2) triglyceride, low density lipoprotein-cholesterol, and HDL cholesterol in mice fed chow, or chow supplemented with 1.3% chloline, 1.3% DMB, or both (SEE FIG. 5). Addition of DMB to mouse diet improved the atherogenic lipoprotein profile of the mice, with significant reductions in atherogenic cholesterol levels (total cholesterol, low density lipoproteins, and triglycerides) and increase in high density lipoproteins).

Example 4

Effect of DMB on Cholesterol Accumulation and Foam Cell Formation

Figure 6:
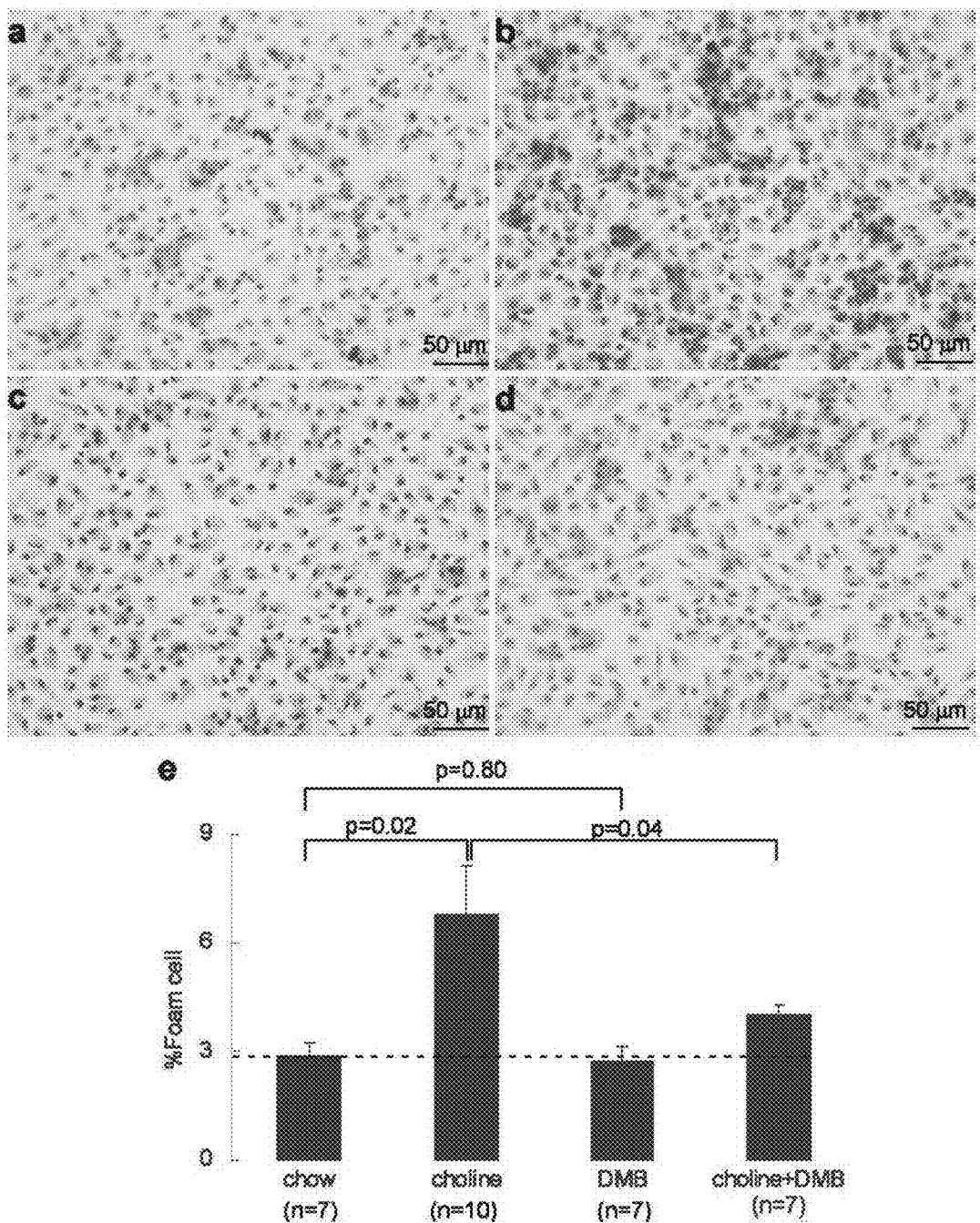
FIGS. 6A-E show staining of peritoneal macrophages from mice fed diets of: (a) chow only, (b) choline supplemented, (c) DMB supplemented, and (d) choline+DMB supplemented. Panel (e) shows calculated foam cell %.

Experiments were conducted during development of embodiments of the present invention to examine the effect of addition of DMB on cholesterol accumulation and foam cell formation. C57BL/6J.Apoe−/− male mice at the time of weaning (4 weeks) were placed on chow diet supplemented with 1.3% choline, 1.3% DMB, both, or neither. Peritoneal macrophages were collected, fixed in 4% paraformaldehyde and stained with oil red 0/hematoxin. Addition of DMB reversed the high choline diet induced cholesterol accumulation and foam cell formation (SEE FIG. 6).

Example 5

Effect of DMB on Total Cholesterol

Figure 7:
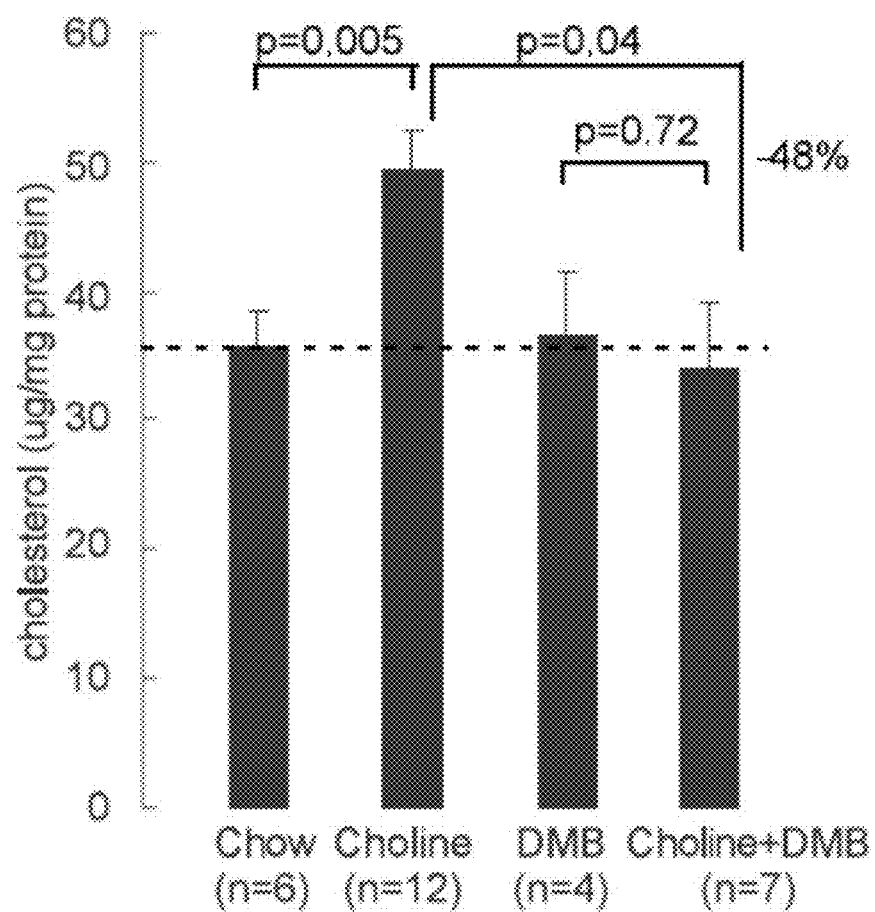
FIG. 7 shows a plot of total cholesterol in peritoneal macrophages recovered from mice at 20 weeks of age. And DMB treatment induced reduction in cholesterol accumulation.

Experiments were conducted during development of embodiments of the present invention to determine the effect of DMB on total cholesterol level in peritoneal mouse macrophages (SEE FIG. 7). C57BL/6J.Apoe−/− male mice at the time of weaning (4 weeks) were placed on chow diet supplemented with 1.3% choline, 1.3% DMB, both, or neither. The total cholesterol of cells was quantified by stable isotope dilution LC/MS/MS. Cells number was quantified by protein content in cell lystates. Significant increases in macrophage cholesterol content induced by a high choline diet were blocked by addition of DMB (SEE FIG. 7). These data indicate a reduction in high choline diet-induced foam cell formation.

Example 6

Effect of DMB on Trimethylamine Generation

Figure 8:
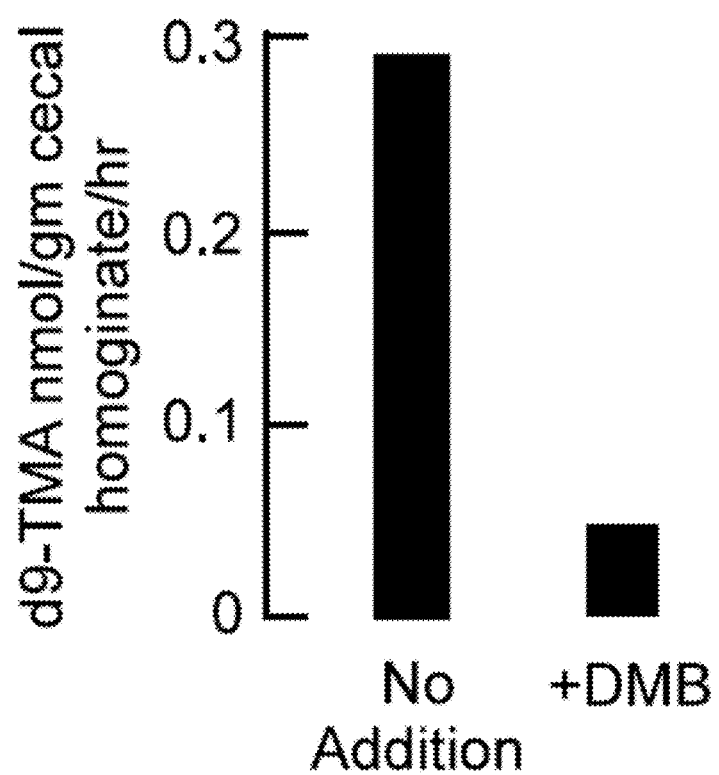
FIG. 8 shows a plot demonstrating DMB administration promotes inhibition of conversion of choline to TMA in vivo.

Experiments were conducted during development of embodiments of the present invention to examine the effect of DMB on intestinal microflora-catalyzed generation of trimethylamine from choline. Mouse celum was homogenized as a source of intestinal microflora. D9-choline was used as a substrate and the generation of d0-TMA was quantified by stable isotope dilution LC/MS/MS. Addition of DMB markedly inhibited gut flora-mediated catabolism of choline to TMA (SEE FIG. 8).

Example 7

DMB and Antibiotics Inhibit TMAO Production and Platelet Aggregation

Experiments were conducted during development of embodiments of the present invention to examine the effect of DMB and antibiotics on suppressing gut flora mediated production of TMAO and on suppressing platelet aggregation.

1) Demonstration that DMB and Antibiotics Inhibits TMA and TMAO Formation In Vivo.

Figure 9:
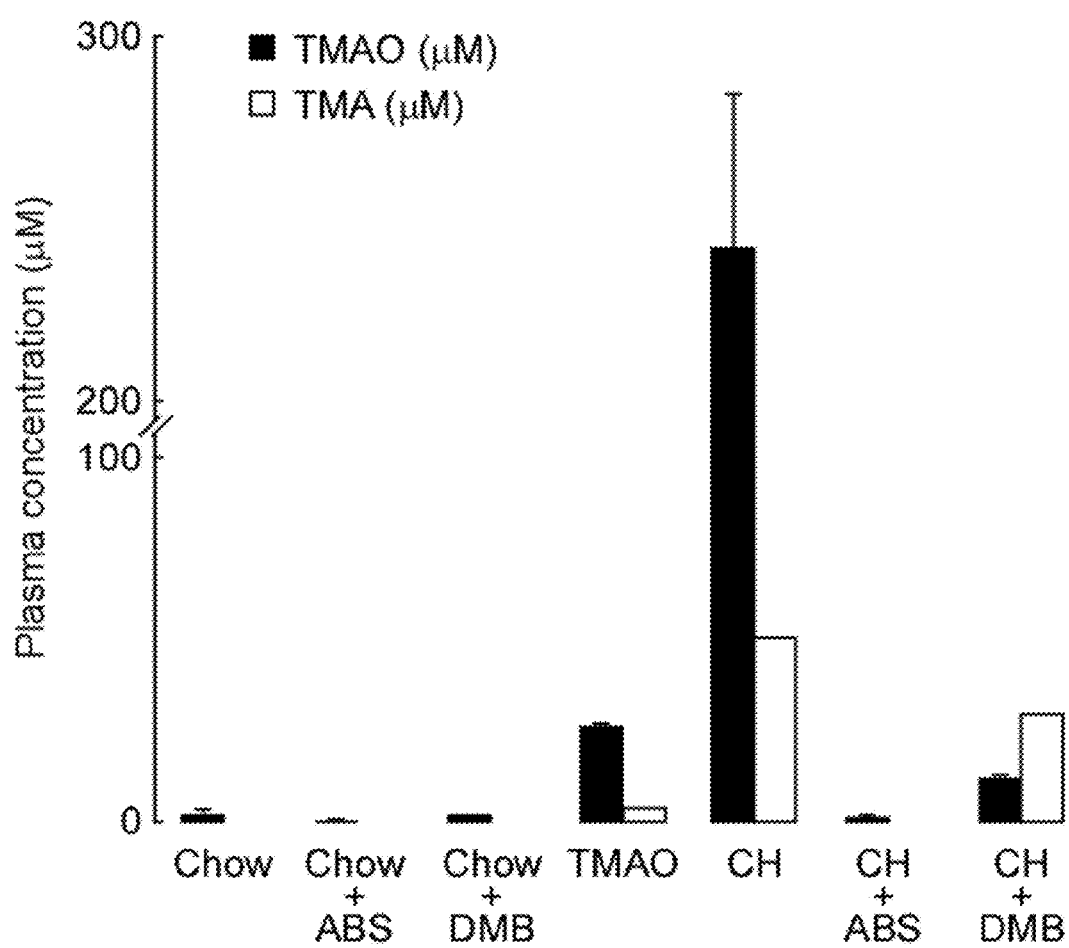
FIG. 9 shows that suppression of intestinal flora with oral broad spectrum antibiotics inhibits TMA and TMAO production, confirming a gut flora requirement for TMA and TMAO formation.

Six week old female mice were placed on the indicated diets+/− shown in FIG. 9, including Chow, CHOW+antibiotics (ABS; which was 0.5 g/L vancomycin, 1 g/L neomycin sulfate, 1 g/L metronidazole, and 1 g/L ampicillin), TMAO, CH (chow supplemented with 1.0% wt/wt choline), CH and ABS, and CH+DMB. Mice were placed on these diets at 6 weeks of age and maintained on the diets for 3 weeks. Plasma was then recovered and both TMA and TMAO were determined by stable isotope dilution LC/MS/MS. Note that a diet rich in choline (similar to a Western diet) leads to increases in plasma TMA and TMAO levels. FIG. 9 shows that suppression of intestinal flora with oral broad spectrum antibiotics inhibits TMA and TMAO production, confirming a gut flora requirement for TMA and TMAO formation. FIG. 9 also shows that DMB inhibits TMA and TMAO formation in the mice on the high choline diet.

2) High Choline Diet Enhances Platelet Aggregation Ex Vivo & Dietary Choline Mediated Platelet Hyper-responsiveness is Inhibited by Suppression of Gut Flora with Oral Antibiotics.

Figure 10:
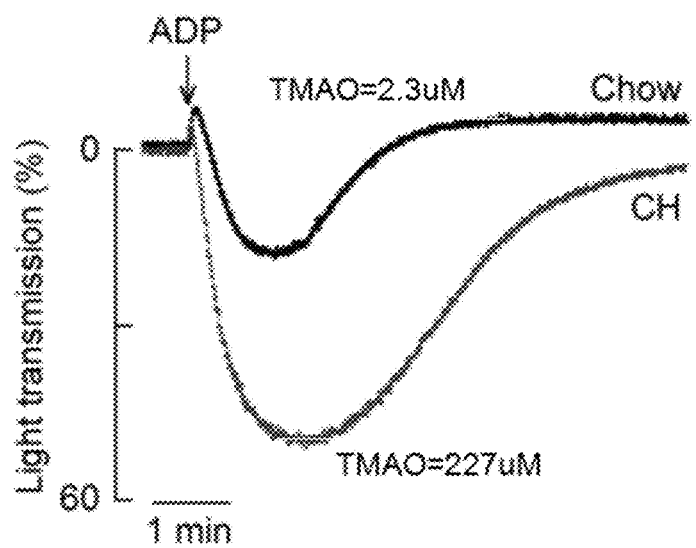
FIG. 10A shows that animals on the high choline diet had enhanced TMAO plasma levels and increased platelet hyperresponsiveness as monitored by increased platelet aggregation to ADP.
FIG. 10B shows that the suppression of plasma TMAO markedly reduces the choline diet induced increases in platelet aggregation.
Figure 10:
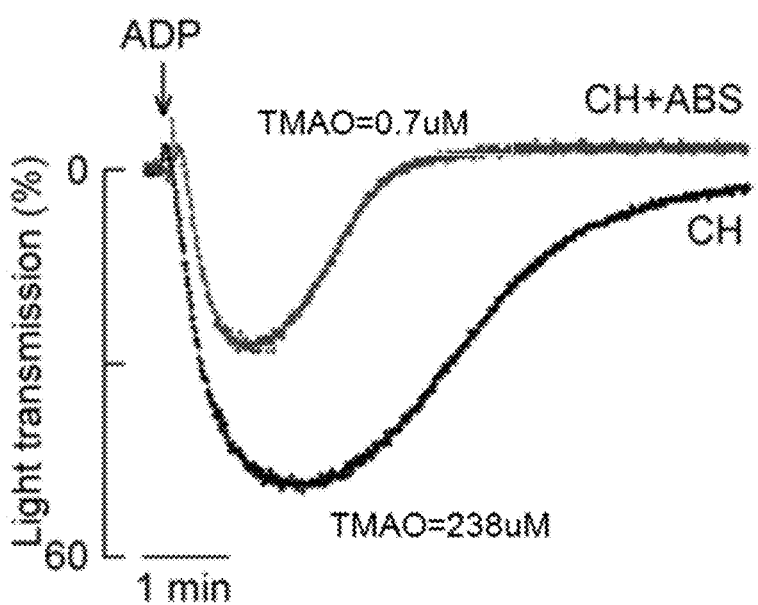

In this example, mice were placed on either normal chow diet at time of weaning, or a high choline diet. After several weeks, whole blood was removed, and platelets isolated. The ability of a submaximal agonist of platelets, ADP, to trigger platelet aggregation was then determined. In parallel, plasma levels of TMAO were determined by established stable isotpe dilution LC/MS/MS analyses. Animals on the high choline diet had enhanced TMAO plasme levels, as shown in FIG. 10A. Importantly, the platelets from these animals also show markedly enhanced platelet aggregation responses. This is a clear signal of a pro-thrombotic phenotype in the mice on a high choline diet. In a similar study, the mice on the high choline were also placed on a cocktail of broad spectrum antibiotics (described above and in Wang et al., Nature 2011, April, 472(7341):57-63, incorporated by reference it its entirety for all purposes) to suppress intestinal microflora, and reduce plasma TMAO levels. As shown in FIG. 10B, the suppression of plasma TMAO markedly reduces the choline diet induced increases in platelet aggregation. These data indicate that a drug that can reduce diet dependent TMAO generation can be anti-thrombotic, reducing platelet hyperresponsiveness. Such drugs (e.g., DMB or antibiotics) are attractive since they should not induce excess bleeding (e.g., like commercial anti-thrombotic drugs like clopidogrel or Warfarin). That is, TMAO only accentuates platelet function, and reducing TMAO levels (like with DMB, antibiotic, or some other drug or approach, be it functional food, probiotic, or prebiotic) would decrease in vivo thrombosis, but not reduce below "normal" function, and thus not increase bleeding risk.

3) Gut Flora Enzyme Inhibitor DMB Inhibits Platelet Hyperrespoinsiveness Induced by Dietary Choline.

Figure 11:
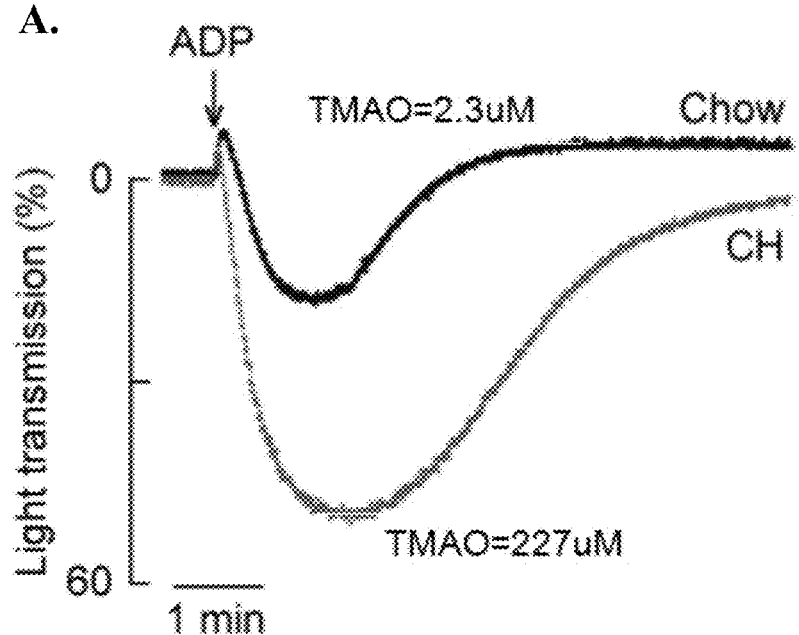
FIG. 11A shows that animals on the high choline diet had enhanced TMAO plasma levels.
FIG. 11B shows that DMB inhibits TMAO formation in the mice and also markedly reduces platelet hyperresponsiveness.
Figure 11:
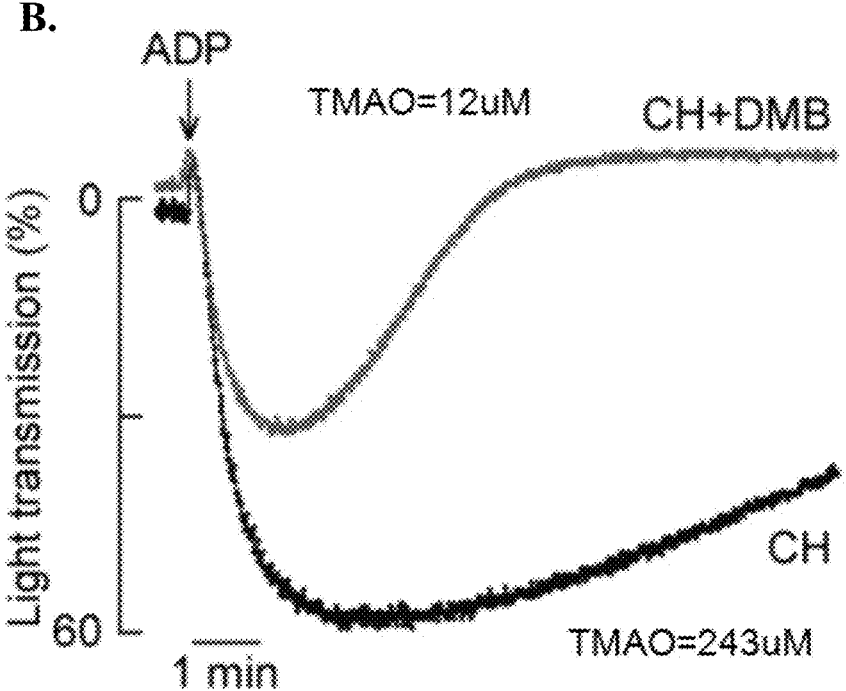

The same experimental design as described for part 2) above was used, but this time one of the mice groups is on a diet supplemented with choline and DMB was given. FIG. 11A shows that animals on the high choline diet had enhanced TMAO plasma levels, and FIG. 11B shows that DMB inhibits TMAO formation in the mice and also markedly reduces platelet hyperresponsiveness.

4) Targeting the Gut Flora Enzyme Responsible for TMAO Formation Inhibits Platelet Hyperresponsiveness from Dietary Choline.

Figure 12:
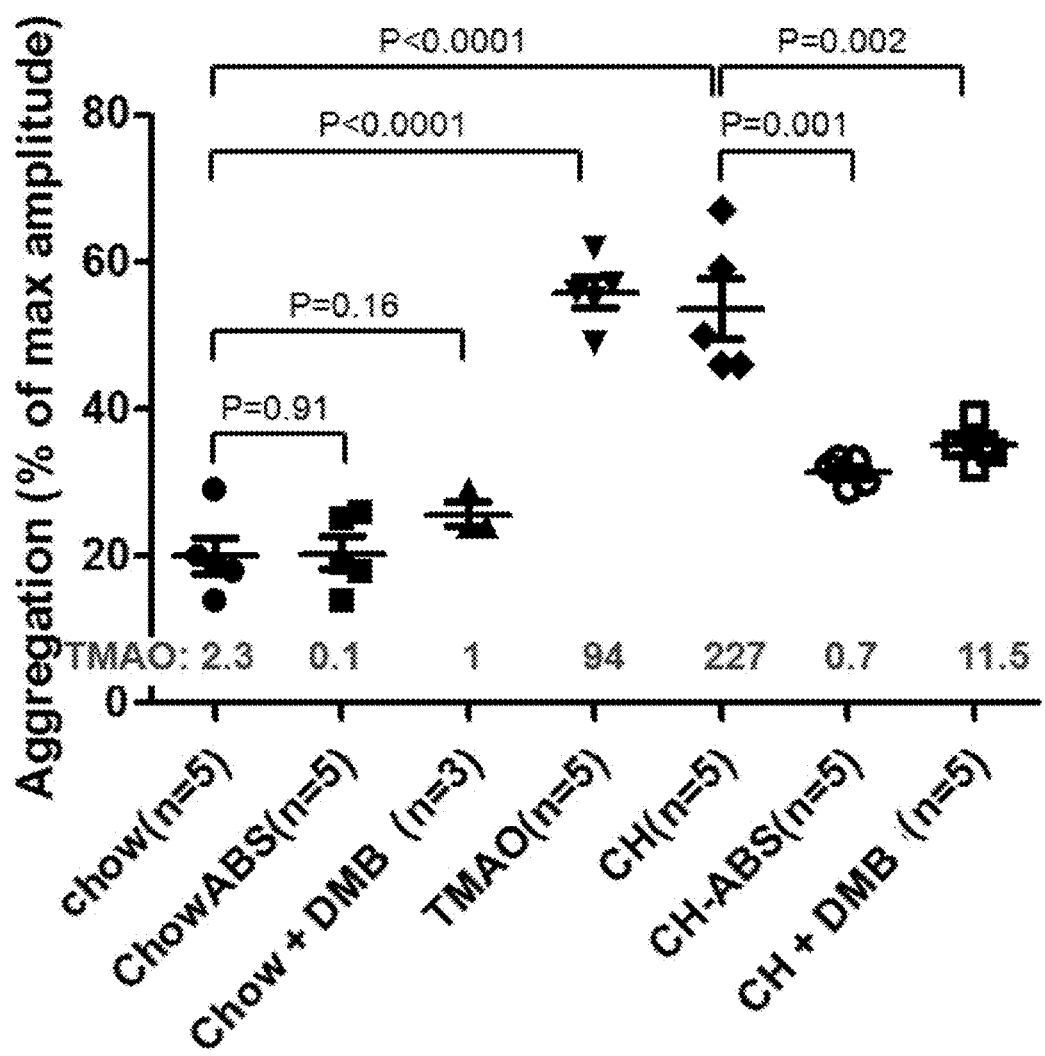
FIG. 12 summarizes data from the groups of mice in Example 7 plus others.

FIG. 12 summarizes data from the groups of mice above. FIG. 12 plots maximum amplitude of platelet aggregation responses vs the indicated diets and treatments (DMB or antibiotic suppression of flora). In summary, FIG. 12 shows that addition of DMB blocks platelet hyper-responsiveness (aggregation) from a high choline diet or endogenous TMAO. FIG. 12 shows that a diet high in choline enhances platelet aggregation rates, but only in the presence of intact intestinal flora, since suppression of flora with antibiotics both prevents TMAO formation, and inhibits diet induced enhancement in platelet aggregation. FIG. 12 further shows that dietary supplementation directly with TMAO promotes enhanced platelet aggregation.

5) TMAO, a Gut Flora Dependent Metabolite of Dietary Choline, Enhances In Vivo Thrombosis Rates in Atherosclerosis Prone ApoE−/− Mice.

Figure 13:
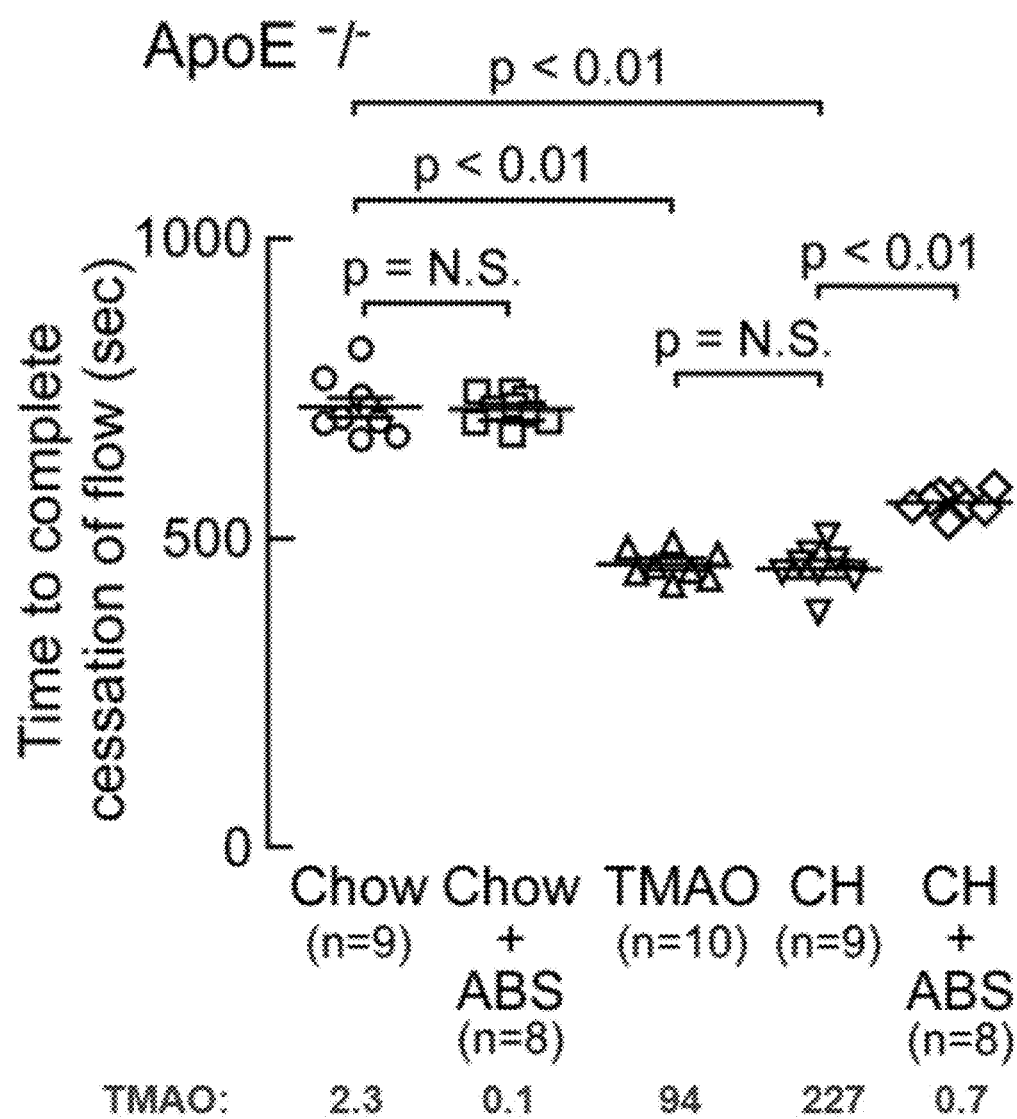
FIG. 13 shows TMAO, a gut flora dependent metabolite of dietary choline or other trimethylamine containing nutrient, enhances in vivo thrombosis rates in vivo. Experiments here are in atherosclerosis prone ApoE−/− mice, and show that antibiotics that inhibit gut flora mediated conversion of choline to TMAO should be useful in promoting reduced thrombosis rates.

In this example, carotid artery in vivo thrombosis rates were determined using vital microscopy on the indicated groups of mice in FIG. 13. Mice were on the indicated diets+/−ABS for 3 weeks. Note that a diet high in choline produces TMAO and accelerates in vivo thrombosis rates, but only in the presence of intact intestinal flora, since suppression of flora with antibiotics both prevents TMAO formation, and inhibits diet induced enhancement in in vivo thrombosis rates. Also note that dietary supplementation directly with TMAO promotes accelerated in vivo thrombosis rates.

The data shown in FIG. 13 indicates that inhibiting TMAO formation should result in reduced thrombosis rates. These studies extend to in vivo studies what was seen before with ex vivo platelet aggregation studies from mice on the various indicated diets. Note that a diet high in choline enhances in vivo thrombosis rates, as monitored by time to cessation of blood flow in the carotid artery. A shorter time indicates faster platelet aggregation (enhanced in vivo thrombosis).

6) TMAO, a Gut Flora Dependent Metabolite of Dietary Choline, Enhances In Vivo Thrombosis Rates in Wild-type Mice.

Figure 14:
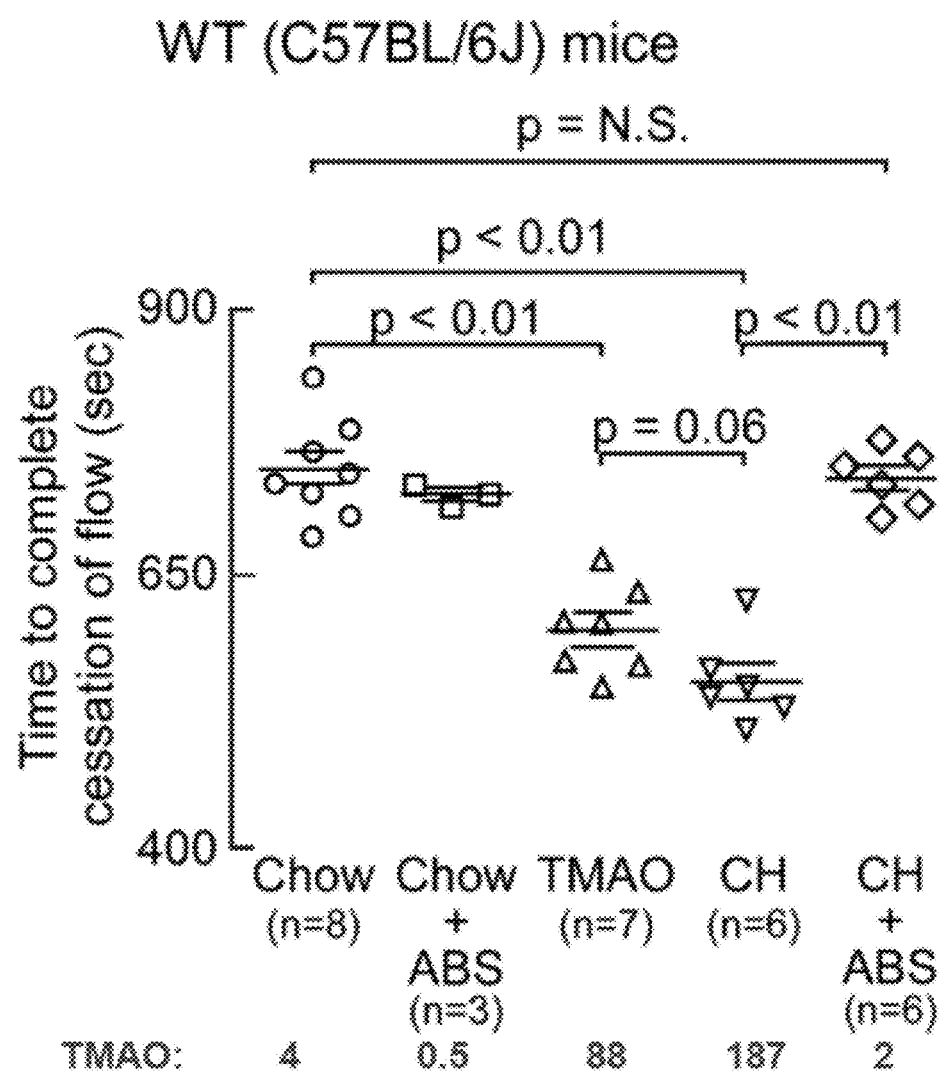
FIG. 14 shows TMAO, a gut flora dependent metabolite of dietary choline, enhances in vivo thrombosis rates in wild-type mice in the absence of dyslipidemia, and that antibiotics or other means of inhibiting gut flora mediated conversion of choline or other dietary trimethylamines into TMA and TMAO should be useful in promoting reduced thrombosis rates.

This example repeats the study immediately above, excepts uses wild-type mice. The results are shown FIG. 14. FIG. 14 indicates that inhibiting TMAO formation in wild-type mice results in reduced thrombosis rates. This is significant because it shows that one does not have to have hyperlipidemia to have the effect of enhanced platelet activation from TMAO.

Figure 15:
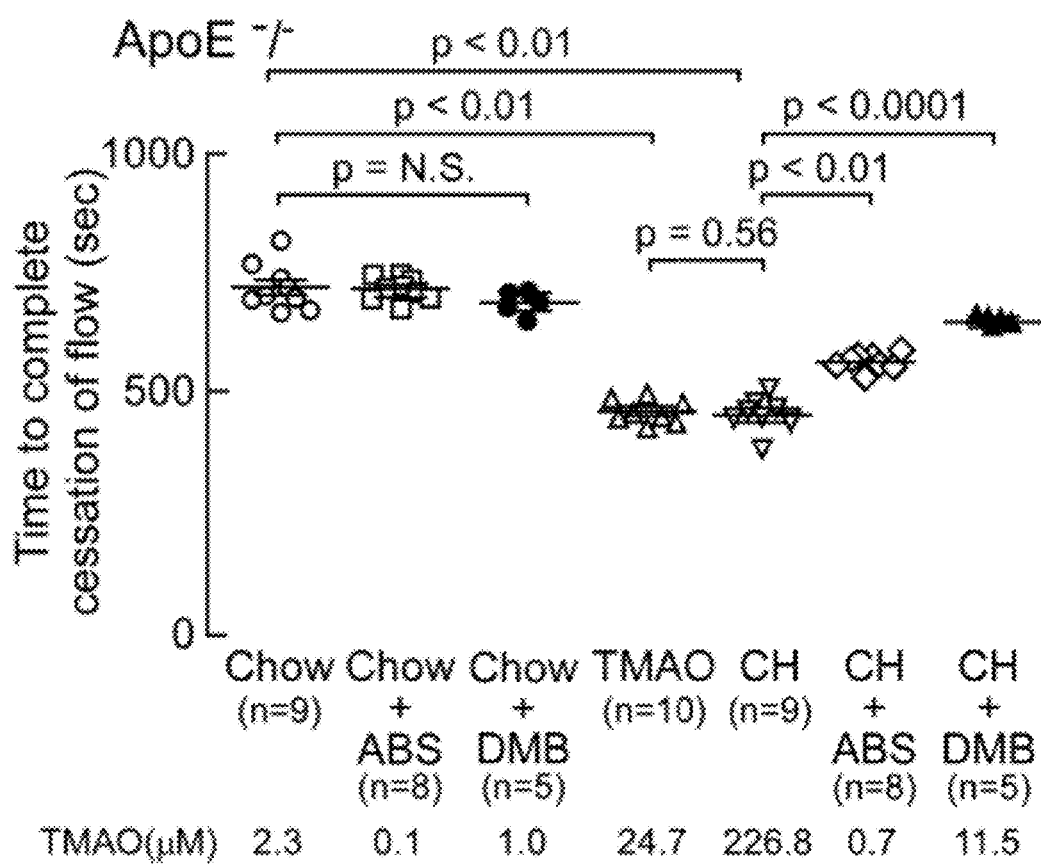
FIG. 15 shows a summary of in vivo thrombosis data in mice in the presence versus absence of either antibiotics or DMB.

7) DMB Inhibits TMAO Mediated Enhancement in In Vivo Thrombosis Rates in WT Mice Carotid artery in vivo thrombosis rates were determined using vital microscopy on the indicated groups of mice shown in FIG. 15. Mice were on the indicated diets+/−ABS or DMB for 3 weeks. FIG. 15 shows a summary of the in vivo thrombosis data in mice in the presence vs absence of either antibiotics or DMB. FIG. 15 shows that DMB and antibodies block the reduction in in vivo thrombosis rates seen on a high choline diet and also block TMAO levels.

Example 8

Gut Flora Metabolism of Phosphatidylcholine Portend Risk of Major Adverse Cardiac Events This Example describes experiments conducted that show that gut flora metabolism of phosphatidylcholine portends risk of major adverse cardiac events, and that antibiotics can be used to suppress such gut flora metabolism (and therefore could be used to prevent cardiac events).

Methods

Study Patients and Design

Two prospective studies approved by the Cleveland Clinic Institutional Review Board are described in this Example. All participants gave written informed consent. The first study represents a cohort (N=40) of healthy volunteers aged >18 years without chronic illness or end-organ dysfunction (including known history of heart failure, renal failure, pulmonary disease, or hematologic diseases), no active infection or received antibiotics, and no use of probiotics. Subjects underwent dietary "phosphatidylcholine (PC) challenge" (see below) during Visit 1. Among them, 6 were given metronidazole 500 mg twice daily plus ciprofloxacin 500 mg once daily for 1 week, and repeat PC challenge performed after antibiotics (Visit 2). A third and final PC challenge was performed ≥one month following cessation of antibiotics and re-acquisition of gut flora (Visit 3).

The second study is comprised of 4,007 stable adult subjects ≥18 years of age undergoing elective diagnostic cardiac catheterization with no evidence of acute coronary syndrome and cardiac troponin I (cTnI)<0.03 ug/L. CVD was defined as documented history of coronary artery disease (CAD), peripheral artery disease, coronary or peripheral revascularization, >50% stenosis on one or more vessels during coronary angiography, or history of either myocardial infarction (MI) or stroke. Creatinine clearance was estimated by the Cockcroft-Gault equation. Routine laboratory tests were measured on the Abbott Architect platform (Abbott Laboratories, Abbott Park Ill.) except for myeloperoxidase, which was determined using the CardioMPO test (Cleveland Heart Labs, Inc., Cleveland, Ohio). Adjudicated outcomes were ascertained over the ensuing 3 years for all subjects following enrollment, including MACE (major adverse cardiac event), such as all-cause mortality, non-fatal MI, or non-fatal stroke.

Dietary Phosphatidylcholine Challenge

A simple dietary PC/choline challenge test was provided to subjects in the form of a known source of PC along with a tracer level of an ingestible deuterium-labeled PC (d9-trimethyl-dipalmitoylphosphatidylcholine chloride [d9-PC]) as standard medical isotopes (under Investigational New Drug exemption). Each "PC challenge" was composed of a blood draw at baseline following an overnight (12-hour) fast and spot random urine collection. At baseline, subjects were provided 2 hard boiled eggs (size large) including yolk (estimated ~250 mg of total choline each) to be eaten within a 10-minute period together with 50 mg of d9-PC in a gelatin capsule. Serial venous blood sampling was performed at 1,2, 3,4,6 and 8 h time points, along with a 24 h urine collection. High purity d9(trimethyl)-PC (>98% isotope enrichment) provided was synthesized from 1-palmitoyl,2-palmitoyl,sn-glycero-3-phosphoethanolamine following exhaustive methylation with d3-methyliodide (Cambridge Isotopes Laboratories Inc, Andover Mass.). d9-PC was isolated by preparative thin layer chromatography and high performance liquid chromatography, crystallized and dried under vacuum, and its purity (>99%) confirmed by multinuclear NMR and mass spectrometry.

Measurements of Choline Metabolites

Plasma aliquots analyzed were isolated from whole blood collected into ethylenediaminetetraacetic acid tubes, maintained at 0-4° C. until processing within 4 hours, and stored at −80° C. An aliquot from 24-hour urine collections was spun to precipitate any potential cellular debris, and supernatants were stored at −80° C. until analysis. TMAO, trimethylamine (TMA), choline, betaine and thier d9-isotopologues were quantified using stable isotope dilution HPLC with on-line electrospray ionization tandem mass spectrometry (LC/EST/MS/MS) methods as recently described using d4(1,1,2,2)-choline, d3(methyl)-TMAO, and d3(methyl)-TMA as internal standards[10]. For measurement of TMA in plasma, samples were acidified (10 mM HCl final) prior to storage at −80 C. Concentrations of TMAO in urine were adjusted for urinary dilution by analysis of urine creatinine concentration.

Statistical Analysis

The Student's t-test and the Wilcoxon-Rank sum test for continuous variables and chi-square test for categorical variables were used to examine the difference between the groups. Plasma TMAO levels were divided into quartiles for analyses. Kaplan-Meier analysis with Cox proportional hazards regression was used for time-to-event analysis to determine Hazard ratio (HR) and 95% confidence intervals (95% CI) for MACE. Logistic regression analyses were performed by adjusting for traditional cardiac risk factors including age, gender, systolic blood pressure, history of diabetes mellitus, low-density and high-density lipoproprotein cholesterol, triglycerides, smoking history, plus BMI, medications, estimated creatinine clearance and plasma hsCRP levels. Improvement in model performance introduced by the inclusion of TMAO was evaluated using net reclassification improvement (NRI) index. C-statistic was calculated using the area under ROC curve. Three-year predicted probabilities of a MACE event were estimated from the Cox model. All analyses were performed using R version 2.8.0 (Vienna, Austria). P values <0.05(two-sided) were considered statistically significant.

Results

TMAO is a Metabolite of Dietary PC in Humans and Gut Flora Plays an Obligatory Role in its Formation.

Figure 4:
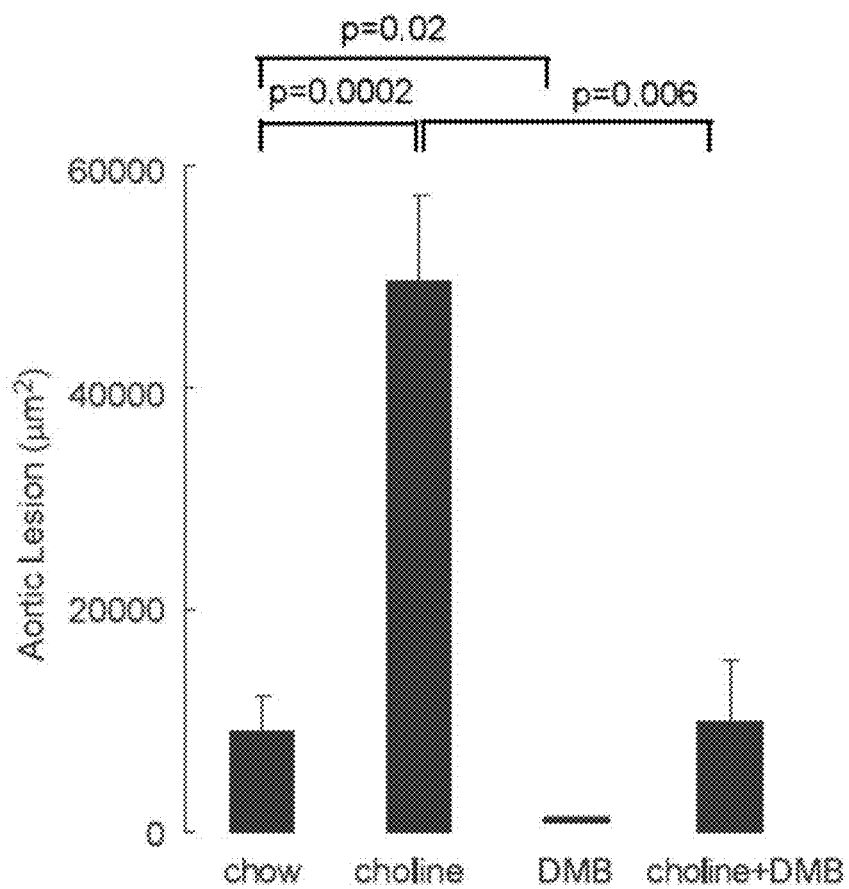
FIG. 4 shows a plot of the effect of diet on the accumulation of aortic lesions, and a reduction in aortic atherosclerotic plaque from dietary choline by DMB administration.
Figure 16:
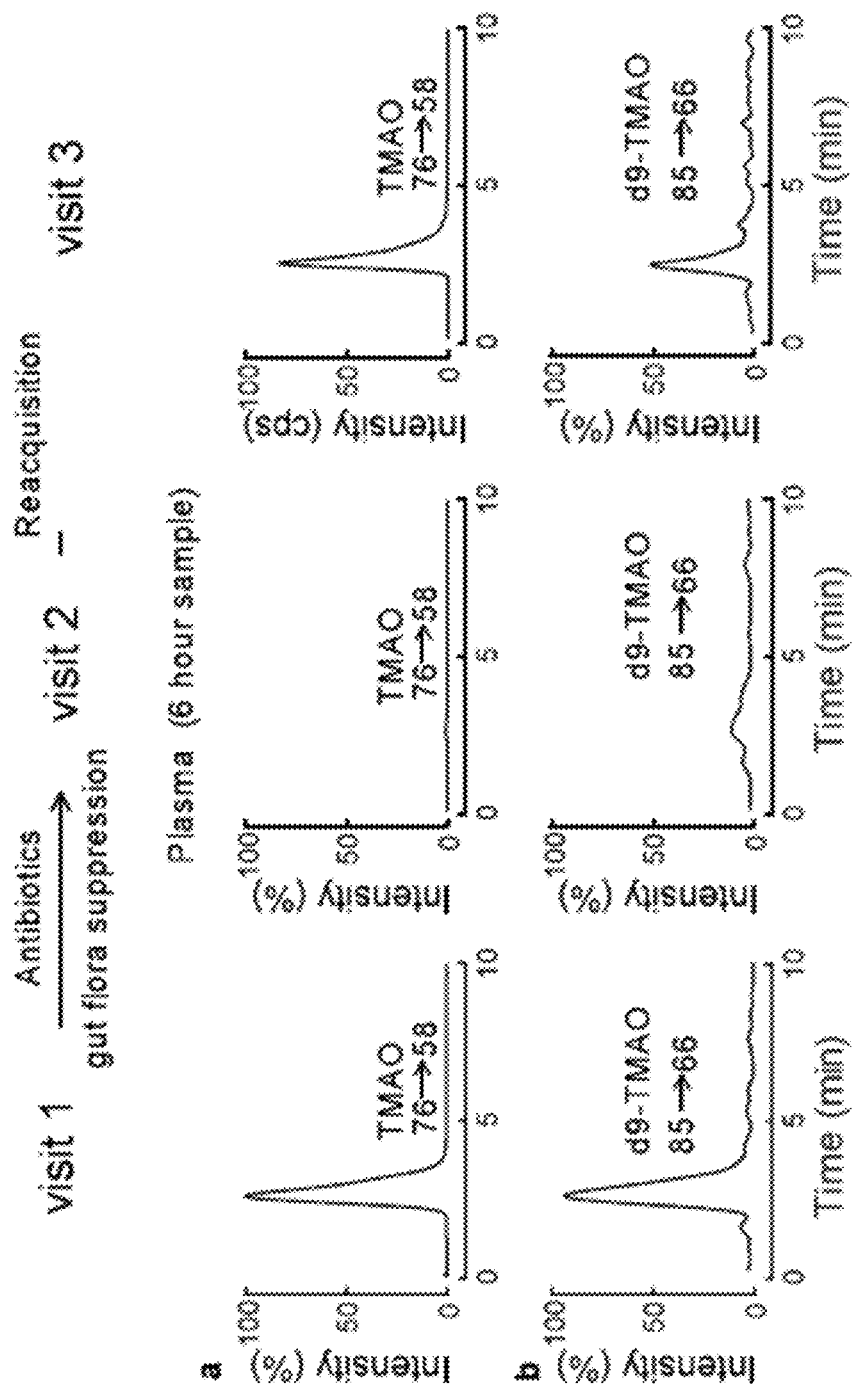
FIGS. 16A-16D show human plasma levels of phosphatidylcholine metabolites (TMAO, Choline, Betaine) after oral ingestion of two hard-boiled eggs and d9-phosphatidylcholine before and after antibiotics.
Figure 16:
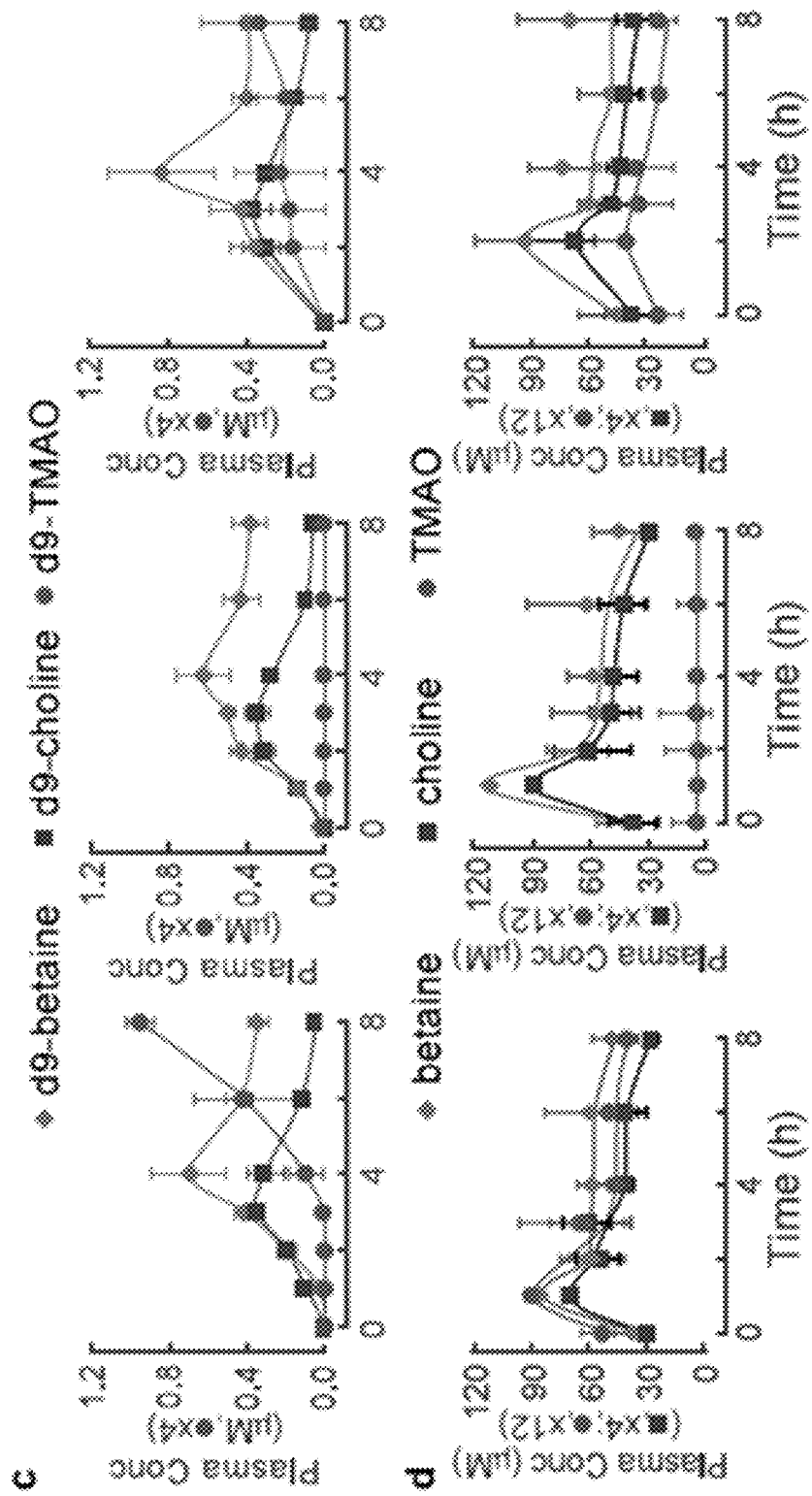
Figure 19:
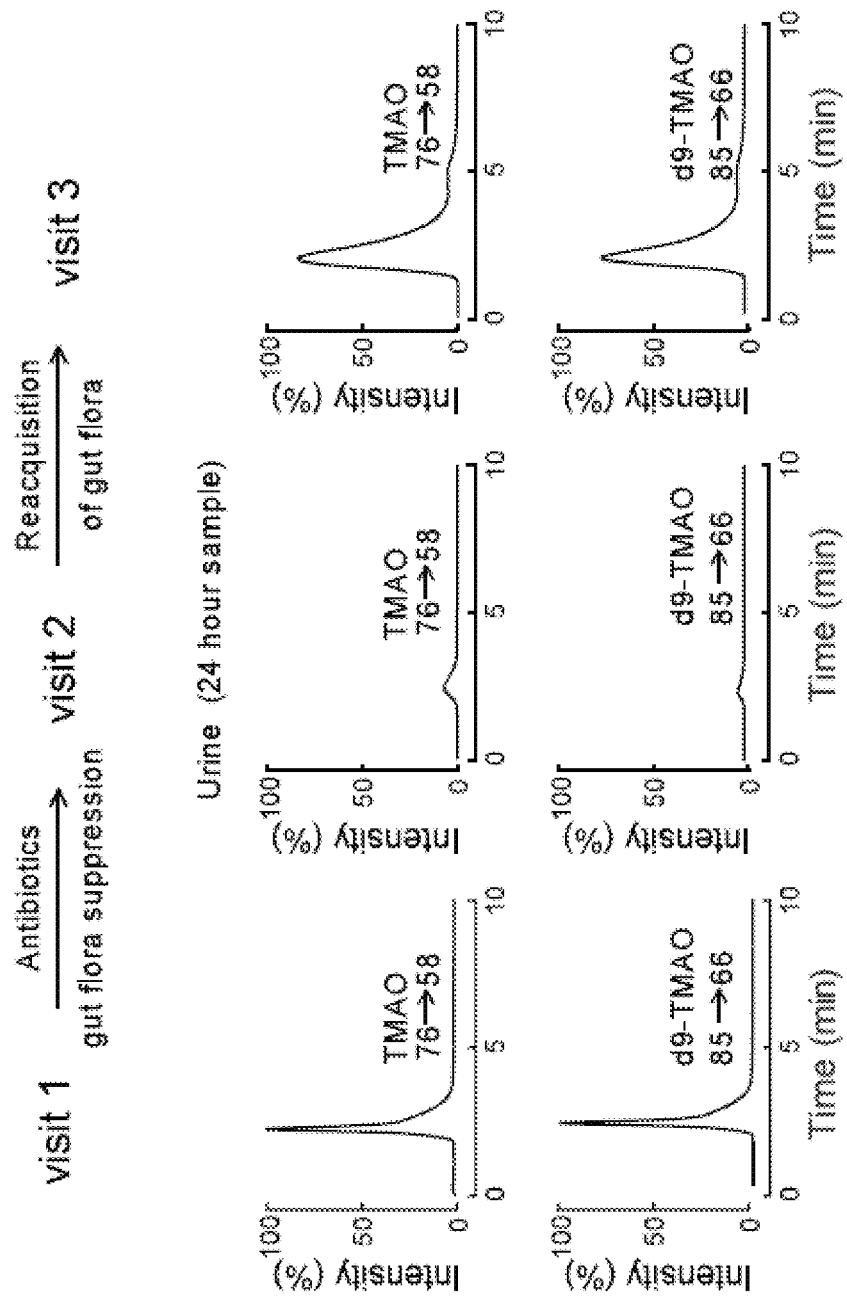
FIG. 19 shows human 24-hour urine levels of TMAO after oral ingestion of two hard-boiled eggs and d9-phosphatidylcholine before and after antibiotics.
Figure 20:
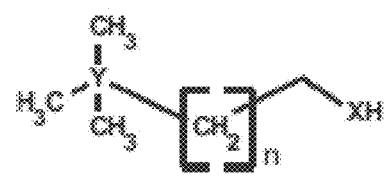
FIG. 20 shows the general structures of nutrient analogue inhibitors of TMA production. The variables in the formula are the same as described for Formula I herein.
Figure 20:
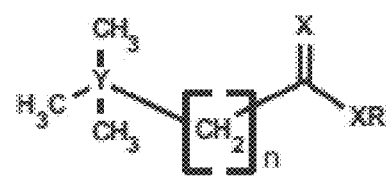
Figure 20:
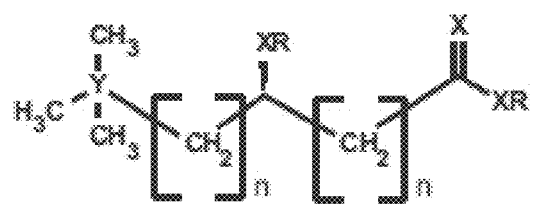
Figure 20:
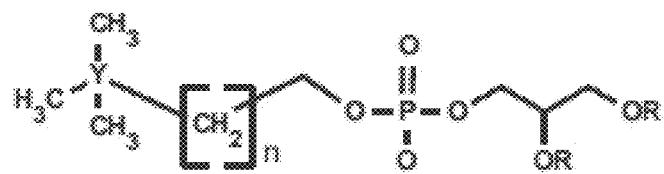
Figure 21A:
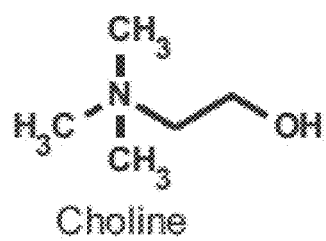
FIGS. 21A and 21B show the chemical structures of choline analogous that could be used as inhibitors of TMA production.
Figure 21A:
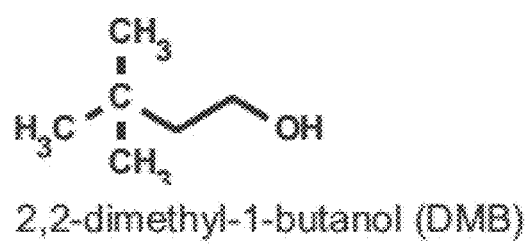
Figure 21A:
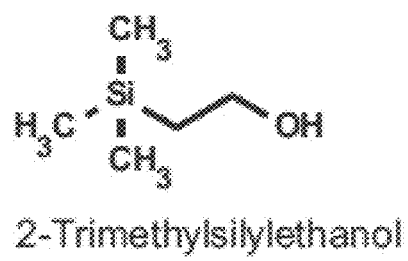
Figure 21A:
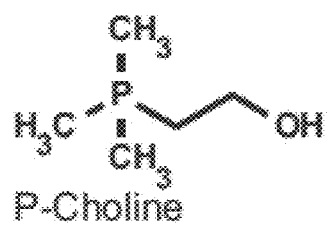
Figure 21A:
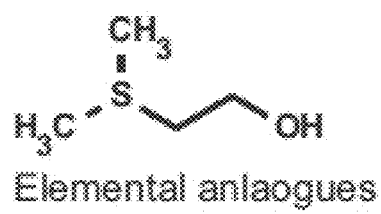
Figure 21B:
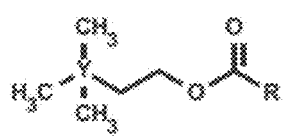
Figure 21B:
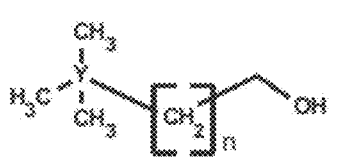
Figure 21B:
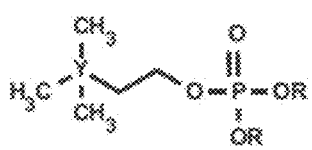
Figure 21B:
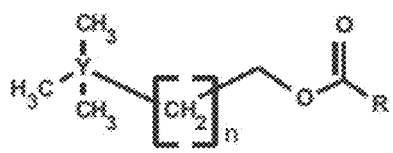
Figure 21B:
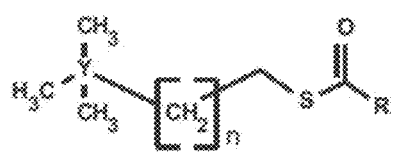
Figure 21B:
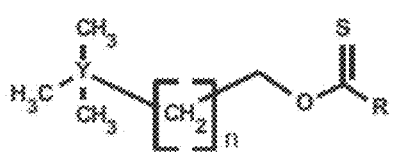
Figure 22A:
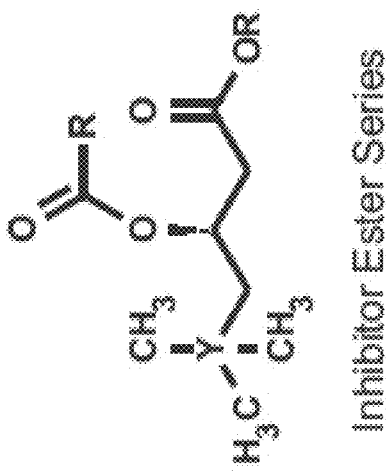
FIGS. 22A and 22B show the chemical structures of carnitine analogues that could be used as inhibitors of TMA production.
Figure 22A:
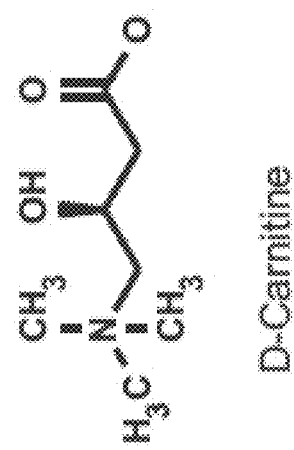
Figure 22A:
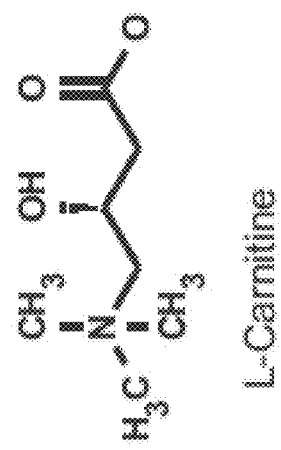
Figure 22B:
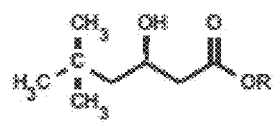
Figure 22B:
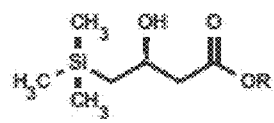
Figure 22B:
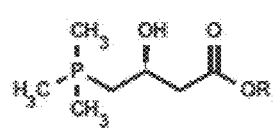
Figure 22B:
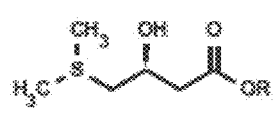
Figure 22B:
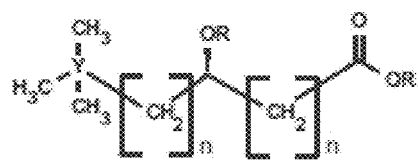
Figure 22B:
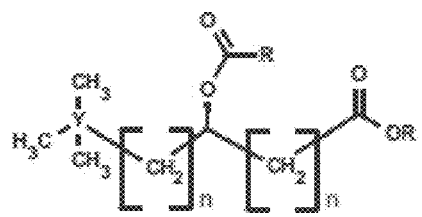
Figure 22B:
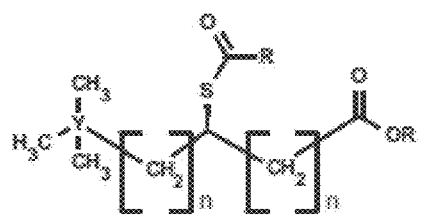
Figure 22B:
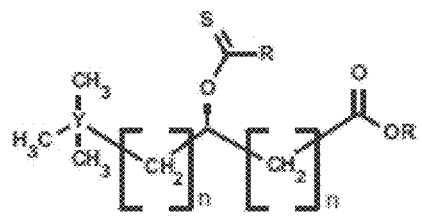
Figure 23:
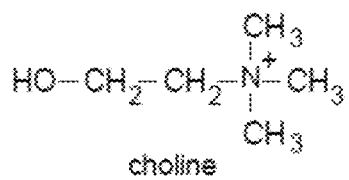
FIG. 23 shows certain choline derivatives that may be used as TMA production inhibitors.
Figure 23:
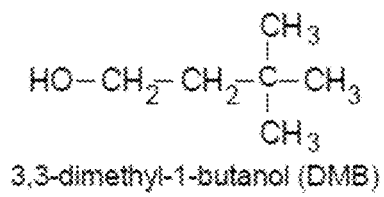
Figure 23:
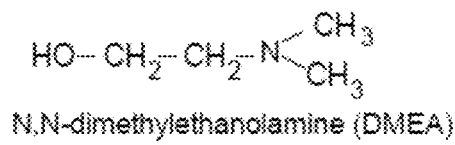
Figure 23:
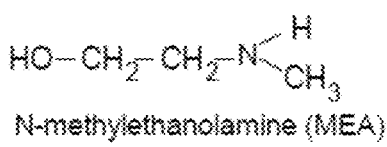
Figure 23:
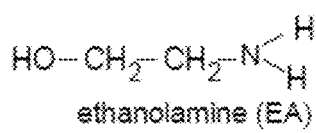
Figure 23:
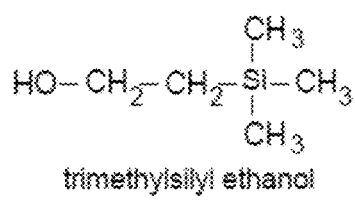
Figure 23:
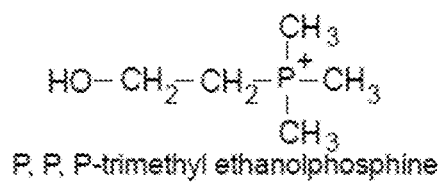
Figure 24:
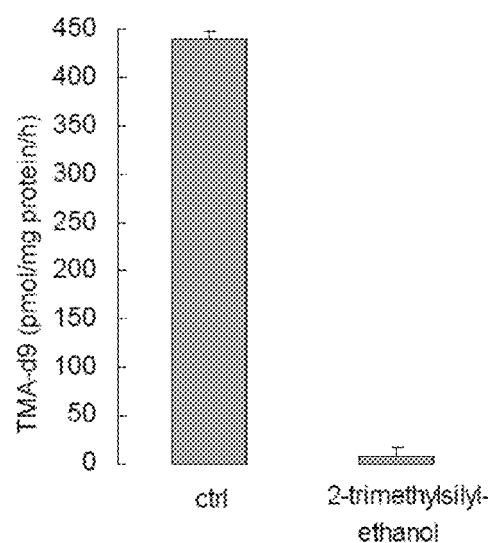
FIG. 24 shows a data plot showing trimethylsilylethanol serves as an inhibitor of TMA production from choline from *proteus mirabilis*.

The major pathway for digestion of dietary PC in humans is via pancreatic lipases, which are secreted into the intestinal lumen and promote cleavage of the fatty acids from the phospholipid, whereupon both glycerophosphocholine and the free fatty acids are absorbed[16,17]. Recent isotope tracer studies in germ-free and conventional mice showed that a quantitatively minor metabolic pathway for dietary PC (and choline) in rodents ultimately produces TMAO, a pro-atherogenic metabolite that requires intestinal microbial flora for its generation[10]. Whether TMAO production in humans requires gut flora had not yet been established. In initial studies, it was therefore sought to determine whether TMAO can originate from dietary PC in subjects, and if so, whether formation of TMAO requires intestinal microflora. Egg yolk is a known dietary source of PC. Following PC challenge, non-labeled TMAO, choline, and betaine were present in fasting plasma at baseline (FIG. 16c), and both TMAO and d9-TMAO were readily detected in plasma following PC/d9-PC ingestion as monitored by LC/MS/MS (FIG. 16a,b). Time-dependent increases in both natural isotope (FIG. 16d) and d9-tracer forms (FIG. 16c) of TMAO, choline and betaine were also observed postprandially. Examination of 24 hour urine specimens following "PC challenge" similarly showed the presence of TMAO and d9-TMAO (FIG. 19). A strong correlation was observed between plasma and both absolute urine TMAO concentrations (Spearman's r=0.58, p<0.001) and urinary TMAO/creatinine ratio (Spearman's r=0.91, p<0.001) in the healthy subject cohort (n=40). Remarkably, suppression of intestinal microflora by taking oral broad spectrum antibiotics for 1 week resulted in complete suppression in detectable TMAO in fasting plasma, as well as either TMAO or d9-TMAO following PC challenge in either plasma (FIG. 16 center (Visit 2)), or 24 hour urine collection (FIG. 19). In parallel analyses, post-prandial elevations in plasma TMA and d9-TMA were observed following PC challenge at visit 1, but were completely suppressed to non-detectable levels following antibiotics. In contrast, the time course for postprandial changes in free choline or betaine (natural abundance and d9-isotopologues) were not altered by suppression of intestinal microflora. Following cessation of antibiotics and reacquisition of intestinal microflora over the ensuing ≥month, PC challenge of volunteers again resulted in readily detectable and time dependent changes in TMAO and d9-TMAO in plasma (FIG. 16) and 24-hour urine collection (FIG. 4). Collectively, these results establish that plasma and urine TMAO (and TMA), as well as free choline and betaine, are all formed as metabolites of dietary PC in humans. These results also reveal an obligatory role for intestinal microflora in the generation of TMA and TMAO, but not choline or betaine, from dietary PC in humans. Finally, these results indicate that intestinal microflora plays a more important role than diet in influencing plasma levels of TMAO, since fed versus fasting state showed only modest changes within an individual, relative to the breadth of fasting plasma levels observed in subjects (see below).

Elevated Plasma Levels of the Gut Flora-dependent Metabolite TMAO Predict Incident Risk for Non-fatal Heart Attack, Stroke and Death.

It was next sought to examine the relationship between fasting plasma levels of TMAO and incident cardiovascular risks in subjects. Table 1 illustrates the baseline characteristics of 4,007 subjects with fasting plasma TMAO levels and long-term cardiovascular outcomes.

TABLE 1

Baseline Characteristics

| Variable | Whole cohort (n = 4,007) | Without Events (n = 3,494) | With Events (n = 513) | P value |
|---|---|---|---|---|
| Age (years) | 63 ± 11 | 62 ± 11 | 68 ± 10 | <0.001 |
| Male Gender (%) | 64 | 65 | 62 | 0.161 |
| Body mass index | 28.7 (25.6-32.5) | 28.7 (25.7-32.5) | 28.1 (24.8-32.4) | 0.033 |
| Diabetes mellitus (%) | 32 | 30 | 43 | <0.001 |
| Hypertension (%) | 72 | 71 | 79 | <0.001 |
| Smoking (%) | 65 | 65 | 69 | 0.053 |
| LDL-c (mg/dL) | 96 (78-117) | 96 (78-117) | 96 (75-116) | 0.337 |
| HDL-c (mg/dL) | 34 (28-41) | 34 (28-41) | 33 (28-40) | 0.034 |
| Triglycerides (mg/dL) | 118 (85-170) | 118 (85-169) | 124 (86-173) | 0.521 |
| ApoB (mg/dL) | 82 (69-96) | 82 (69-96) | 82 (68-96) | 0.862 |
| ApoA1 (mg/dL) | 116 (103-133) | 117 (103-133) | 114 (100-129) | 0.002 |
| Fasting glucose | 102 (93-119) | 102 (92-117) | 106 (94-135) | <0.001 |
| hsCRP (ng/L) | 2.4 (1-5.9) | 2.3 (1-5.5) | 3.9 (1.8-9.8) | <0.001 |
| MPO (pM) | 115.2 (76.4-245.7) | 113.2 (75.4-238.3) | 136.3 (84.7-329.3) | <0.001 |
| eGFR(ml/min/1.73 m$^2$) | 82 (69-95) | 83 (71-96) | 75 (56-89) | <0.001 |
| Total leukocyte count (WBC, x10$^9$) | 6.1 (5.1-7.5) | 6.1 (5-7.5) | 6.4 (5.3-8.1) | 0.001 |
| Baseline drugs (%): | | | | |
| Aspirin | 74 | 74 | 70 | 0.038 |
| ACE inhibitors | 50 | 49 | 58 | <0.001 |
| Statin | 60 | 61 | 56 | 0.057 |
| Beta blockers | 63 | 63 | 65 | 0.414 |
| TMAO (μM) | 3.7 (2.4-6.2) | 3.5 (2.4-5.9) | 5 (3-8.8) | <0.001 |

Values expressed in mean ± standard deviation or median (interquartile range).
Abbreviations:
LDL-c, low-density lipoprotein cholesterol;
HDL-c, high-density lipoprotein cholesterol;
ApoB, apolipoprotein B;
ApoA1, apolipoprotein A1;
hsCRP, high sensitivity C-reactive protein;
MPO, myeloperoxidase;
WBC, white blood cell;
ACE, angiotensin converting enzyme;
TMAO, trimethylamine N-oxide The cohort examined represents an intermediate risk population undergoing elective cardiac evaluations with relatively well controlled fasting lipid profile and preserved renal function (Table 1). Compared to the lowest quartile, the highest quartile had a 2.5-fold increased risk (HR 2.5, 95% CI 2.0-3.2; p<0.001, Table 2).

TABLE 2

Unadjusted and adjusted hazard ratio for risks of MACE at 3-years stratified by quartile levels of TMAO

| | TMAO (range) | | | |
|---|---|---|---|---|
| | Quartile 1 | Quartile 2 | Quartile 3 | Quartile 4 |
| Range | <2.43 | 2.43-3.66 | 3.67-6.18 | ≥6.18 |
| | Major adverse cardiac events (Death, myocardial infarction, stroke) | | | |
| Unadjusted HR | 1 | 1.22 (0.91-1.63) | 1.53 (1.16-2.01)** | 2.51 (1.95-3.24)** |
| Adjusted HR | | | | |
| Model 1 | 1 | 1.12 (0.84-1.50) | 1.28 (0.97-1.70) | 1.85 (1.42-2.42)** |
| Model 2 | 1 | 1.05 (0.76-1.44) | 1.15 (0.84-1.58) | 1.55 (1.14-2.12)** |

Figure 17:
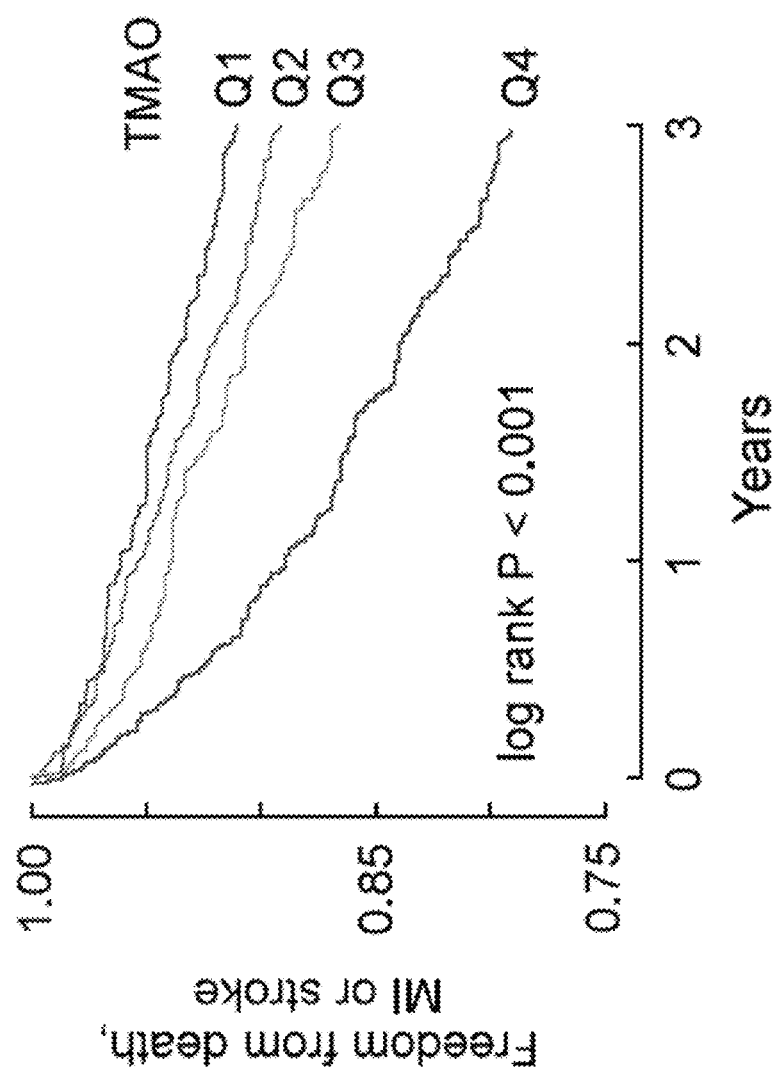
FIG. 17 shows Kaplan-Meier estimates of long-term major adverse cardiac events, according to TMAO quartiles.

**$p < 0.01$;
HR, Hazard ratio.
Cox Proportional Hazards analyses variables were adjusted to +1 standard deviation increment for continuous variables.
Model 1: Adjusted for traditional risk factors (age, gender, smoking, systolic blood pressure, low density lipoprotein cholesterol (LDL), high-density lipoprotein cholesterol (HDL), and diabetes mellitus), plus log-transformed hsCRP
Model 2: Adjusted for traditional risk factors, plus log-transformed hsCRP, myeloperoxidase, log-transformed estimated GFR, total leukocyte count, body mass index, aspirin, statins, ACE inhibitors and beta blockers A graded risk increase for MACE associated with increasing TMAO levels is clearly illustrated in the Kaplan-Meier analysis shown in FIG. 17. When the endpoints were analyzed separately, higher TMAO level still conferred significantly higher risk of death (HR 3.2, 95% CI 2.1-4.8; p<0.001) and non-fatal MI or stroke (HR 2.3, 95% CI 1.5-3.6; p<0.001) at 3-year follow-up. After adjusting for traditional risk factors, hsCRP, eGFR, and other inflammatory/metabolic covariates, elevated plasma TMAO levels remained a significant increased risk of incident MACE at 3 years (Table 2). Inclusion of TMAO resulted in a significant improvement in risk estimation over traditional risk factors (NR 18.6%, p<0.001; IDI 9.2%, p<0.001; C-statistic 68.3% vs 66.4%, p=0.01). In a separate analysis, subject were excluded that underwent revascularization within the 30-days following enrollment in the study. In this sub-cohort (n=3,475), TMAO remained significantly associated with incident MACE risk (Q4 vs Q1, unadjusted HR(95% CI), 2.47 (1.87-3.27); adjusted HR(95% CI) 1.79 (1.34-2.4); both p<0.001).

Elevated Plasma Levels of the Gut Flora Metabolite TMAO Predict Increased MACE Risk in Relatively Lower Risk Cohorts.

Figure 18:
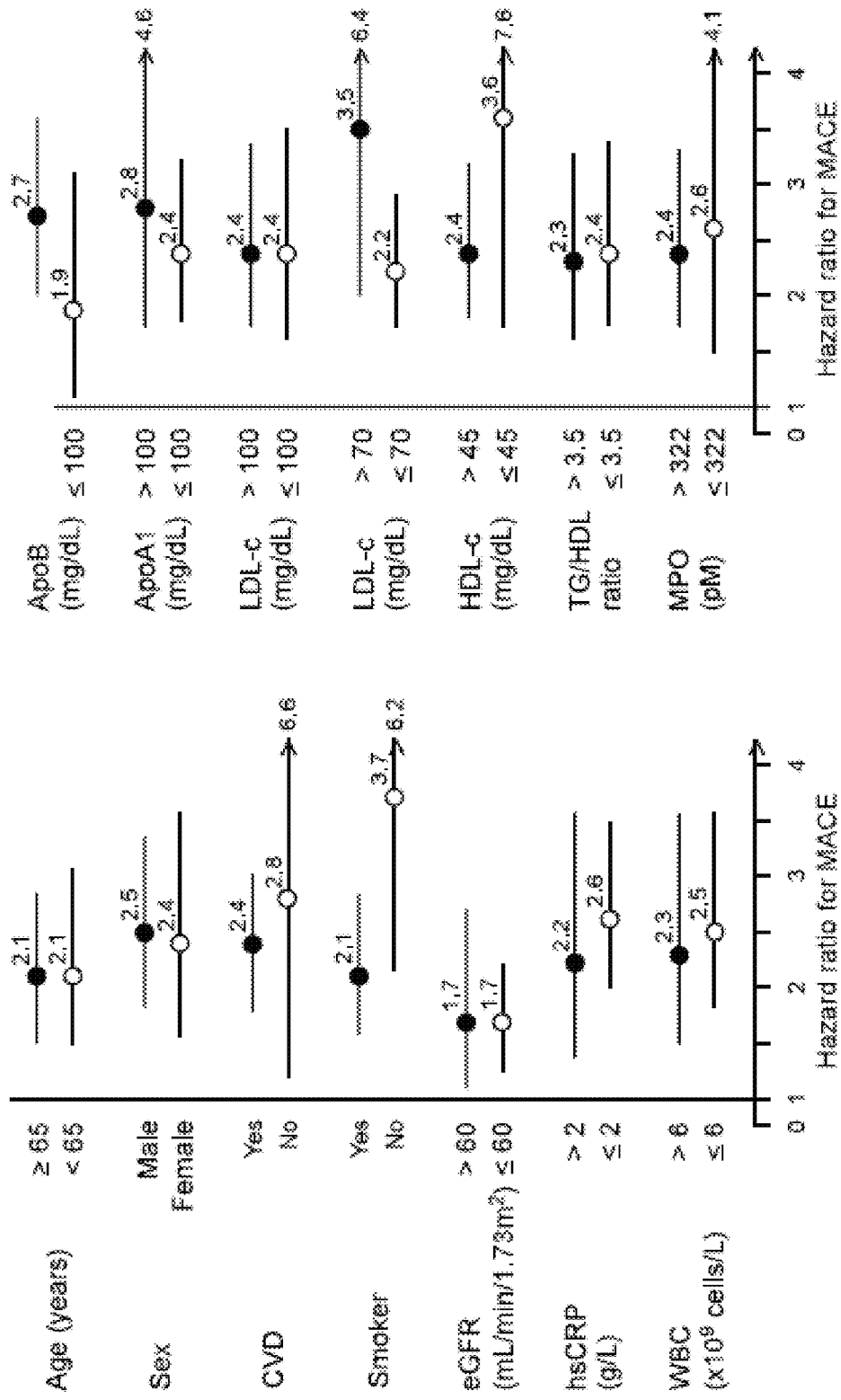
FIG. 18 shows risks of major adverse cardiac events among patient subgroups, according to baseline TMAO levels. Hazard ratios were comparing top to bottom quartiles. TMAO predicts increased risk of major adverse cardiac events in multiple low risk cohorts otherwise not identified as being at risk from traditional risk factors.

The prognostic value of elevated plasma TMAO levels remained significant in various subgroups associated with reduced overall cardiac risks (FIG. 18), including those who are younger, among females, those without known history of CVD or CAD risk equivalents, those with lipids treated to aggressive treatment goals, or those with normal blood pressure, non-smokers, or among those with lower levels of other known cardiac/inflammation risk markers such as hsCRP, myeloperoxidase, or white blood cell count (FIG. 18).

Discussion

Since its discovery in 1856, choline and TMAO metabolism have been extensively studied in both animals and humans[4,11,18,19,20]. Recent animal model studies with germ free mice indicate a role for gut flora in atherosclerosis in the setting of a diet rich in PC/choline via formation of the metabolite TMA and conversion to TMAO[10] (herein incorporated by reference in its entirety). Although it has been demonstrated that gut flora contributes to the production of TMA/TMAO in animals, participation of gut flora in making TMAO from dietary PC in humans has not been established. This example demonstrates the generation of the pro-atherogenic metabolite TMAO from dietary PC in humans through use of stable isotope tracer feeding studies. This example further demonstrates a role for gut flora in production of TMAO in humans via both its suppression with oral broad spectrum antibiotics, and then reacquisition of TMAO following cessation of antibiotics and intestinal recolonization. Finally, this example demonstrates the potential clinical prognostic significance of this gut flora generated metabolite by showing that fasting plasma TMAO levels predict future development of MACE independent of traditional cardiovascular risk factors, and within multiple lower risk subgroups, including both primary prevention subjects, and subjects with more aggressive LDL cholesterol or apolipoprotein B goals. The present findings point to the important contributions of gut flora dependent pathway(s) in the pathophysiology of atherosclerotic CAD in humans, and indicate that antibiotic treatment would be useful for treating or preventing CAD and related conditions (e.g., thrombosis).

The importance of intestinal microflora in complex metabolic diseases like obesity has become widely recognized by several seminal studies[6-9,21,22]. The ability of oral broad-spectrum antibiotics to temporarily suppress gut flora and TMAO production is a direct demonstration that gut flora plays an obligatory role in TMAO production from PC/choline in humans. Gut flora converts the choline moiety of dietary PC into TMA, which is subsequently converted into TMAO by hepatic FMOs[16,24]. A requirement for TMA to be converted into TMAO by hepatic FMOs[25] may help to explain the observed delay in the detection of d9-TMAO levels following oral ingestion of d9-PC, since separate analyses monitoring TMA and d9-TMA production shows a time course consistent with a precursor→product relationship. Interestingly, TMAO has been identified in fish as an important osmolite,[26] and fish ingestion raises urinary TMAO levels. Nevertheless, the high correlation between urine and plasma TMAO levels argues for effective urinary clearance of TMAO as a means of removing nitrogenous waste. Hence, an efficient excretion mechanism for TMAO may thus be protective in preventing the accumulation of TMAO like other "uremic toxins," and does not undermine the mechanistic link between TMAO and cardiovascular risk.

While an association between infectious etiology and atherosclerosis has previously been postulated, studies looking at the role of antimicrobial therapy in preventing disease progression have been disappointing[27,28]. It is important to recognize that the choice of antimicrobial therapy (e.g. azithromycin) was largely based on targeting postulated organisms (e.g. *Chlamydia pneumonae*) rather than modulating gut flora composition or their metabolites. The observations in this example between higher levels of TMAO and incident cardiovascular risk in the present study cohort confirms a direct link between gut flora-host interactions in PC/choline metabolism and cardiovascular phenotypes from animal models to humans. Instead of eradicating pathogenic microbes with an antibiotic, the present findings imply that plasma TMAO levels may potentially identify a relatively conserved gut flora pathway amenable to therapeutic modulation. Thus, recognition of the involvement of intestinal microflora in the development of atherosclerosis suggests multiple new potential avenues for therapeutic intervention. For example, there is clear benefit for maintaining sufficient while limiting excessive consumption of dietary PC, such as through adoption of a more vegan and high fiber containing diet, as this can potentially modulate gut flora composition and reduce total choline intake[21]. Indeed, part of standard dietary recommendations, if adopted, will limit PC and choline-rich foods since these are typically high in fat and cholesterol content[3]. Alternatively, interventions targeting gut flora modulation should play an important additive role in cardiovascular disease prophylaxis, either with a "functional food" such as a probiotic[22], or even a pharmacologic intervention. This latter intervention could take the form of either an inhibitor to block specific gut flora mediated pathways, or even a short course of non-systemic antibiotics to reduce the "burden" of TMAO-producing microbes, as seen in the treatment of irritable bowel syndrome[29].

REFERENCES

1. Executive Summary of The Third Report of The National Cholesterol Education Program (NCEP) Expert Panel on Detection, Evaluation, And Treatment of High Blood Cholesterol In Adults (Adult Treatment Panel III). JAMA 2001; 285:2486-97.
2. Kathiresan S, Melander O, Anevski D, et al. Polymorphisms associated with cholesterol and risk of cardiovascular events. N Engl J Med 2008; 358:1240-9.
3. Patterson K Y, Bhagwat S A, Williams J R, Howe J C, Holden J M. USDA Database for the Choline Content of Common Foods. Release Two.

4. Zhang A Q, Mitchell S C, Smith R L. Dietary precursors of trimethylamine in man: a pilot study. Food Chem Toxicol 1999; 37:515-20.
5. Zeisel S H. Choline: critical role during fetal development and dietary requirements in adults. Annu Rev Nutr 2006; 26:229-50.
6. Gill S R, Pop M, Deboy R T, et al. Metagenomic analysis of the human distal gut microbiome. Science 2006; 312:1355-9.
7. Dumas M E, Barton R H, Toye A, et al. Metabolic profiling reveals a contribution of gut microbiota to fatty liver phenotype in insulin-resistant mice. Proc Natl Acad Sci USA 2006; 103:12511-6.
8. Wen L, Ley R E, Volchkov P Y, et al. Innate immunity and intestinal microbiota in the development of Type 1 diabetes. Nature 2008; 455:1109-13.
9. Backhed F, Ding H, Wang T, et al. The gut microbiota as an environmental factor that regulates fat storage. Proc Natl Acad Sci USA 2004; 101:15718-23.
10. Wang Z, Klipfell E, Bennett B J, et al. Gut flora metabolism of phosphatidylcholine promotes cardiovascular disease. Nature 2011; 472:57-63.
11. de la Huerga J, Popper H. Urinary excretion of choline metabolites following choline administration in normals and patients with hepatobiliary diseases. J Clin Invest 1951; 30:463-70.
12. Simenhoff M L, Saukkonen J J, Burke J F, Wesson L G, Schaedler R W. Amine metabolism and the small bowel in uraemia. Lancet 1976; 2:818-21.
13. Ihle B U, Cox R W, Dunn S R, Simenhoff M L. Determination of body burden of uremic toxins. Clin Nephrol 1984; 22:82-9.
14. Bain M A, Formasini G, Evans A M. Trimethylamine metabolic, pharmacokinetic and safety aspects. Curr Drug Metab 2005; 6:227-40.
15. Erdmann C C. On the Alleged Occurrence of Trimethylamine in the Urine. J Biol Chem 1910; 8:57-60.
16. Li Z, Vance D E. Phosphatidylcholine and choline homeostasis. J Lipid Res 2008; 49:1187-94.
17. Vance D E. Boehringer Mannheim Award lecture. Phosphatidylcholine metabolism: masochistic enzymology, metabolic regulation, and lipoprotein assembly. Biochem Cell Biol 1990; 68:1151-65.
18. Dessaignes M. Trimethylamin aus menschenharn. J L Ann Chem 1856; 100:2-8.
19. Prentiss P G, Rosen H, Brown N, Horowitz R E, Malm O J, Levenson S M. The metabolism of choline by the germ-free rat. Arch Biochem Biophys 1961; 94:424-9.
20. Al-Waiz M, Mikov M, Mitchell S C, Smith R L. The exogenous origin of trimethylamine in the mouse. Metabolism 1992; 41:135-6.
21. Stella C, Beckwith-Hall B, Cloarec O, et al. Susceptibility of human metabolic phenotypes to dietary modulation. J Proteome Res 2006; 5:2780-8.
22. Martin F P, Wang Y, Sprenger N, et al. Probiotic modulation of symbiotic gut microbial-host metabolic interactions in a humanized microbiome mouse model. Mol Syst Biol 2008; 4:157.
23. Loscalzo J. Lipid metabolism by gut microbes and atherosclerosis. Circ Res 2011; 109:127-9.
24. Lang D H, Yeung C K, Peter R M, et al. Isoform specificity of trimethylamine N-oxygenation by human flavin-containing monooxygenase (FMO) and P450 enzymes: selective catalysis by FMO3. Biochem Pharmacol 1998; 56:1005-12.
25. Al-Waiz M, Mitchell S C, Idle J R, Smith R L. The relative importance of N-oxidation and N-demethylation in the metabolism of trimethylamine in man. Toxicology 1987; 43:117-21.
26. Yancey P H, Rhea M D, Kemp K M, Bailey D M. Trimethylamine oxide, betaine and other osmolytes in deep-sea animals: depth trends and effects on enzymes under hydrostatic pressure. Cell Mol Biol (Noisy-le-grand) 2004; 50:371-6.
27. Cannon C P, Braunwald E, McCabe C H, et al. Antibiotic treatment of *Chlamydia pneumoniae* after acute coronary syndrome. N Engl J Med 2005; 352:1646-54.
28. Grayston J T, Kronmal R A, Jackson L A, et al. Azithromycin for the secondary prevention of coronary events. N Engl J Med 2005; 352:1637-45.
29. Pimentel M, Lembo A, Chey W D, et al. Rifaximin therapy for patients with irritable bowel syndrome without constipation. N Engl J Med 2011; 364:22-32.

Although the invention has been described in connection with specific embodiments, it should be understood that the invention as claimed should not be unduly limited to such specific embodiments. Indeed, various modifications of the described modes for carrying out the invention understood by those skilled in the relevant fields are intended to be within the scope of the following claims.

We claim:

1. A method for reducing TMAO (trimethylamine N-oxide) plasma levels in a subject comprising:
   a) identifying a subject as having increased platelet aggregation and/or elevated TMAO levels, and
   b) administering to said subject a composition comprising trimethylsilyl ethanol under conditions such that plasma TMAO levels are reduced in said subject.

2. The method of claim 1, further comprising administering a prebiotic, probiotic, and/or fiber to said subject.

3. The method of claim 1, wherein said identifying comprises viewing results of a platelet aggregation assay performed on a sample from said subject which shows increased platelet aggregation.

4. The method of claim 1, wherein said identifying comprises viewing results of a TMA (trimethylamine) or TMAO assay performed on a sample or exhaled breath from said subject which show elevated TMA or TMAO levels.

5. The method of claim 1, wherein said composition reduces the risk of cardiovascular disease and/or thrombosis when administered to a subject.

6. A method of reducing TMAO plasma levels in a subject comprising administering to a subject a composition comprising trimethylsilyl ethanol under conditions such that plasma TMAO levels are reduced in said subject.

7. The method of claim 6, wherein said subject has been determined to have increased platelet aggregation.

8. The method of claim 6, wherein said subject has been determined to have an elevated TMAO level or an elevated TMA level as indicated by a breath test.

9. The method of claim 6, wherein said administering is under such conditions that at least one symptom of said cardiovascular disease and/or thrombosis is reduced or eliminated.

10. The method of claim 6, further comprising administering a probiotic, a prebiotic, and/or fiber to said subject.

11. The method of claim 6, wherein said composition is co-administered with one or more agents which provide therapy for cardiovascular disease.

12. The method of claim 11, wherein said one or more agents comprises one or more antibiotics that target gut flora.

* * * * *